(12) United States Patent
Shin et al.

(10) Patent No.: US 9,044,044 B2
(45) Date of Patent: Jun. 2, 2015

(54) IMMUNE ACTIVATION OF GREEN TEA HYDROLYSATE AND METHOD FOR PREPARING FOOD COMPOSITION CONTAINING THE SAME

(75) Inventors: Kwang-Soon Shin, Seongnam-si (KR); Hyung-Joo Suh, Seoul (KR); Kwang-Won Yu, Cheongju-si (KR); Tae-Young Kim, Ansan-si (KR)

(73) Assignee: BIONIC TRADING CORPORATION, Ansan-Si, Gyeonggi-Do (KR)

( * ) Notice: Subject to any disclaimer, the term of this patent is extended or adjusted under 35 U.S.C. 154(b) by 123 days.

(21) Appl. No.: 13/282,256

(22) Filed: Oct. 26, 2011

(65) Prior Publication Data
US 2012/0270833 A1 Oct. 25, 2012

(30) Foreign Application Priority Data
Apr. 25, 2011 (KR) .......................... 10-2011-0038682

(51) Int. Cl.
*A61K 31/732* (2006.01)
*C08B 37/06* (2006.01)
*A23L 1/30* (2006.01)
*C08B 37/00* (2006.01)

(52) U.S. Cl.
CPC ............. *A23L 1/3002* (2013.01); *C08B 37/006* (2013.01); *A61K 31/732* (2013.01); *C08B 37/0087* (2013.01); *C12Y 302/01015* (2013.01); *A23V 2002/00* (2013.01)

(58) Field of Classification Search
None
See application file for complete search history.

(56) References Cited

U.S. PATENT DOCUMENTS

| 8,128,966 B2 * | 3/2012 | Staples et al. .................. 424/725 |
| 2009/0280215 A1 * | 11/2009 | Yotsumoto ....................... 426/52 |
| 2013/0064858 A1 * | 3/2013 | Albers et al. ................ 424/278.1 |

FOREIGN PATENT DOCUMENTS

| CN | 1699586 | * 11/2005 | .............. C12P 17/06 |
| KR | 10-0700912 B1 | 3/2007 | |
| KR | 10-2010-0026835 A | 3/2010 | |
| WO | JP2004-141056 | * 5/2004 | ................ A23F 3/06 |

OTHER PUBLICATIONS

English translation of JP2004-141056 (May 2004).*
Ekouna et al., "Chemical characterization of pectin from green tea (*Camellia sinensis*)" Carbohydrate Polymers (2011) vol. 83 pp. 1232-1239.*
Stevi, "Zen Green Tea Liqueur and the Matcha Cocktail" Dec. 11, 2008, downloaded from www.twoatthemost.com/zen-green-tea-liqueur.*
English machine translation of CN1699586, (2005) downloaded from http://translationportal.epo.org.*
"Green and Personalized Foods" Program and Poster for Presentation, 2010 International Symposium and Annual Meetng, Hotel Inter-Burgo, Daegu, Korea, Oct. 27-29, 2010, 8 pages.
Wei, X., et al., "Composition and Biological Activity of Tea Polysaccharides Obtained by Water Extraction and Enzymatic Extraction", Lat. Am. J. Pharm. 29 (1), pp. 117-121, (2010).

* cited by examiner

*Primary Examiner* — Eric Olson
(74) *Attorney, Agent, or Firm* — Nath, Goldberg & Meyer; Joshua B. Goldberg; Katelyn J. Bernier

(57) ABSTRACT

Disclosed are an immune-boosting food composition containing a green tea hydrolysate as an active component, and a method for preparing the same.

5 Claims, 13 Drawing Sheets

IMMUNE ACTIVATION OF GREEN TEA HYDROLYSATE AND METHOD FOR PREPARING FOOD COMPOSITION CONTAINING THE SAME

CROSS-REFERENCE TO RELATED APPLICATION

This application claims the benefit under 35 U.S.A. §119 of Korean Patent Application No. 10-2011-0038682, filed on Apr. 25, 2011 in the Korean Intellectual Property Office, the entirety of which is incorporated herein by reference.

BACKGROUND OF THE INVENTION

1. Field of the Invention

The present invention relates to an immune-boosting food composition containing a green tea hydrolysate as an active component and a method for preparing the same.

2. Description of the Related Art

Green tea from leaves of *Camellia sinensis* L. is the most widely consumed tea throughout the world, which contains a variety of nutrients such as polyphenols, polysaccharides and vitamins and is known to be effective in reducing the risk of a variety of diseases. For example, polyphenol present in green tea is receiving considerable attention as a main active component of green tea. In particular, epigallocatechin gallate (EGCG) is known to exhibit a variety of biological activities such as antioxidant and antiarteriosclerotic activities. For this reason, research associated with green tea is mostly focused on EGCG of young leaves which is suitable for preparation of green tea.

However, it is not considered that EGCG is the sole component in charge of the pharmaceutical activities found in green tea and the possibility of presence of other substances having biological activities such as polysaccharides in mature leaves of green tea still remains. Meanwhile, pectin is a polysaccharide mainly present in primary cell walls and middle lamella of high plants, which is a promising material which will exhibit superior action as a source of dietary fiber and physiological effects. Pectin was known as a polymer (α-D-1,4-polygalacturonic acid) in which a plurality of molecules of D-galacturonic acid (GalA) are bonded to one another at an α-1,4 linkage. However, since the detailed structure of pectin was recently found through structural analysis technologies, it has been reported that pectin is mainly composed of homogalacturonan (HG), but has a structure in which homogalacturonans (HG) are covalently bonded to rhamnogalacturonans (RG) in which oligosaccharides and polysaccharides are branch-bonded (FIG. 1).

The inventors of the present invention discovered that fractions obtained by hydrolyzing young and mature leaves of green tea commonly used for drinking with a specific enzyme exhibit immune boosting and anticancer effects. The present invention has been completed based on this discovery.

SUMMARY OF THE INVENTION

Therefore, the present invention has been made in view of the above problems, and it is an object of the present invention to provide an immune-boosting food composition and a method for preparing the same.

In accordance with an aspect of the present invention, the above and other objects can be accomplished by the provision of an immune-boosting food composition containing a hydrolysate of young leaves of green tea used for drinking and mature leaves of green tea not used for drinking (hereinafter, referred to as "green tea hydrolysate") as an active component and a method for preparing the same.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
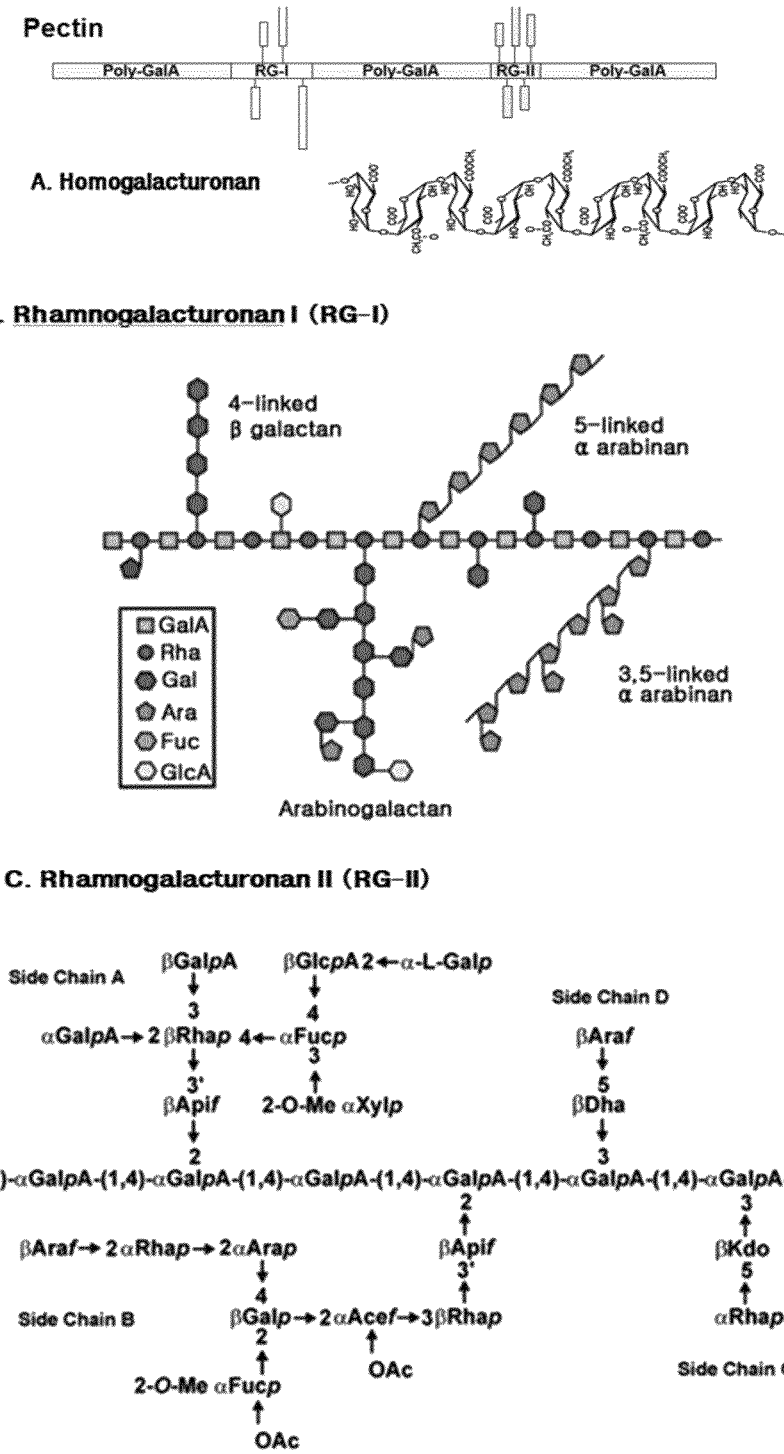
FIG. 1 shows the structure of pectin and constituent components thereof, i.e., homogalacturonan (hereinafter, referred to as "HG"), rhamnogalacturonan I (hereinafter, referred to as RG-I) and rhamnogalacturonan II (hereinafter, referred to as RG-II))

Hereinafter, the present invention will be described in detail. The present invention provides an immune-boosting food composition containing a green tea hydrolysate as an active component.

Also, the present invention provides an immune-boosting food composition containing RG-I or RG-II as an active component.

Also, the present invention provides a method for boosting immune function comprising administering an enzymatic hydrolysate of green tea, or a food composition containing an enzymatic hydrolysate of green tea as an active component to a subject.

In addition, the present invention provides a method for boosting immune function comprising administering rhamnogalacturonan I, rhamnogalacturonan II, or a food composition containing rhamnogalacturonan I and/or rhamnogalacturonan II as an active component to a subject.

Also, the present invention provides a method for preparing an immune-boosting food composition comprising hydrolyzing green tea with an enzyme containing pectinase.

Also, the present invention provides a method for preparing an immune-boosting food composition comprising separating RG-I or RG-II polysaccharides from plants.

Also, the present invention provides a food composition for preventing and treating cancers containing enzymatic hydrolysates of green tea as an active component.

Also, the present invention provides a food composition for preventing and treating cancers containing RG-I or RG-II polysaccharides of green tea as an active component.

Also, the present invention provides a method for preparing a food composition for preventing and treating cancers, the method comprising hydrolyzing green tea with an enzyme containing pectinase.

Also, the present invention provides a method for preparing a food composition for preventing and treating cancers, the method comprising separating RG-I or RG-II polysaccharides from plants.

Also, the present invention provides a pharmaceutical composition for boosting immune function and inhibiting cancers containing an enzymatic hydrolysate of green tea as an active component.

Also, the present invention provides a pharmaceutical composition for boosting immune function and inhibiting cancers containing RG-I or RG-II polysaccharide as an active component.

Also, the present invention provides a method for preventing, treating, reducing and inhibiting cancers, comprising administering an enzymatic hydrolysate of green tea, or a pharmaceutical composition containing an enzymatic hydrolysate of green tea as an active component to a patient.

Also, the present invention provides a method for preventing, treating, reducing and inhibiting cancers, comprising administering rhamnogalacturonan I, rhamnogalacturonan II, or a pharmaceutical composition containing rhamnogalacturonan I and/or rhamnogalacturonan II as an active component to a patient.

Also, the present invention a method for preparing a pharmaceutical composition for boosting immune function and inhibiting cancers, the method comprising hydrolyzing green tea with an enzyme containing pectinase.

Also, the present invention provides a method for preparing a pharmaceutical composition for boosting immune function and inhibiting cancers, the method comprising separating RG-I or RG-II polysaccharide from plants.

Hereinafter, the present invention will be described in detail.

The green tea of the present invention is *Camellia sinensis* L. Preferably, the green tea of the present invention is a mature or young leaf of green tea, more preferably, the green tea of the present invention is a young leaf of green tea.

The enzyme of the present invention is a hydrolase which is capable of hydrolyzing green tea. The enzyme of the present invention is selected from the group consisting of cellulase, pectinase, hemicellulase, arabinase, β-glucanase and xylanase. More preferably, the enzyme of the present invention is pectinase. The green tea enzymatic hydrolysate of the present invention contains RG-I or RG-II polysaccharide as an active component.

The inhibition of cancers means prevention, reduction, treatment and metastasis inhibition of cancers. Preferably, the inhibition of cancers means metastasis inhibition of cancers.

The cancers are not particularly limited in the present invention. Examples of cancers include, but are not limited to lung cancer, ovarian cancer, pancreatic cancer, colon cancer, stomach cancer, large intestine cancer, prostate cancer, thyroid cancer, brain tumor, liver cancer, breast cancer, uterine cancer, testicular cancer, renal cancer, cholangiocarcinoma, leukemia, gastrointestinal cancer, cervical cancer, urological cancer, esophageal cancer, malignant lymphoma, neuroblastoma, maxillary cancer, oral cancer, bladder cancer, hematopoietic neuroblastoma, cell carcinoma and villus cancer.

The pharmaceutical composition of the present invention may be administered to patients who have deteriorated immune functions and cancer patients, or to those who have deteriorated immune functions and are thus susceptible to disease.

The pharmaceutical composition of the present invention may contain 0.01 to 80 parts by weight of the green tea enzymatic hydrolysate, or RG-I or RG-II polysaccharide, preferably 0.02 to 65 parts by weight, based on 100 parts by weight of the composition. However, this content may be varied depending on the demand of patients and depending on conditions such as diet, nutritive conditions, progress of diseases, and brain disorders of patients.

The pharmaceutical composition of the present invention may be administered orally or parenterally and may be used in the form of a general medicine formulation. Preferred pharmaceutical formulations include formulations for oral administration such as tablets, hard or soft capsules, liquids, and suspensions. These pharmaceutical formulations may be prepared using a pharmaceutically acceptable common carrier, for example, formulations for oral administration, using an adjuvant, a binder, a disintegrating agent, a preservative or an extending agent or the like.

A dosage of the pharmaceutical composition containing the green tea enzymatic hydrolysate of the present invention may be determined by medical experts depending on various factors such as conditions, age, gender and complications of patients, but is generally 0.1 mg to 10 g per kg in adults, preferably 10 mg to 5 g per kg in adults. In addition, a unit formulation may contain a daily dose of the pharmaceutical composition or ½, ⅓ or ¼ thereof and may be administered one to six times daily. However, for administration for a long period of time for the purpose of health and hygiene, or health control, the dosage may be lower than the range defined above and the active component may be used in an amount higher than the range defined above since it has no problem in terms of safety.

Meanwhile, the dosage of the pharmaceutical composition containing RG-I or RG-II polysaccharide of the present invention may be determined by medical experts depending on various factors such as conditions, age, gender and complications of patients, but is generally 0.001 mg to 5.0 g per kg in adults, preferably 0.01 mg to 1 g per kg in adults. In addition, a unit formulation may contain a daily dose of the pharmaceutical composition or ½, ⅓ or ¼ thereof and may be administered one to six times daily. However, for administration for a long period of time for the purpose of health and hygiene, or health control, the dosage may be lower than the range defined above.

Examples of the food in the present invention include, but are not limited to, natural foods, processed foods and general food suppliers which contain green tea enzymatic hydrolysate or RG-I or RG-II polysaccharide of the present invention. The food composition of the present invention may be used alone or in combination with other foods or food compositions and may be suitably used by a common method. The amount of active component may be suitably determined according to intended purpose (prevention, reduction and therapeutic treatment). Generally, the green tea enzymatic hydrolysate or RG-I or RG-II polysaccharide of the present invention may be added in an amount of 0.1 to 70 parts by weight, preferably 2 to 50 parts by weight with respect to 100 parts by weight of the total amount of a food or drink during preparation of the food or drink. An effective dose of the green tea enzymatic hydrolysate and RG-I or RG-II polysaccharide may depend on the effective dose of the pharmaceutical composition. However, for administration for a long period of time for the purpose of health and hygiene, or health control, the dosage may be lower than the range defined above and the active component may be used in an amount out of the range defined above since it has no problem in terms of safety.

The type of foods is not particularly limited. The food composition may be used in the form of a formulation for oral administration such as a tablet, a hard or soft capsule, a liquid or a suspension. The formulation may be prepared using an acceptable common carrier, for example, for formulation for oral administration, using an adjuvant, a binder, a disintegrating agent, a lubricant, a solubilizer, a suspending agent, a preservative or an extending agent or the like.

Examples of the food which contains green tea enzymatic hydrolysates or RG-I or RG-II polysaccharide include, but are not limited to, meats, sausages, breads, chocolates, candies, snacks, cookies, pizzas, ramen, other noodles, gums, dairy products including ice creams, a variety of soups, beverages, teas, drinks, alcoholic beverages and vitamin complexes, and other nutritional supplements.

Now, the present invention will be described in more detail with reference to the following Examples and Test Examples. These examples are only provided to illustrate the present invention and should not be construed as limiting the scope and spirit of the present invention.

Materials and Method

Materials

The green tea used in this test was prepared from mature or young leaves of green tea harvested in Hadong-gun in Gyeongsangnam-do available from Hadong County Office. Commercially available Econase™ CE, Rapidase™, Viscozyme™, Celluclast™ 1.5L, Pectinex™, Rohament™ CL, Ultraflo™ L, Cytolase™ PCL 5 and Pectinase™ were used to hydrolyze green tea powders. The manufacture company and characteristics of the enzymes are shown in Table 1.

TABLE 1

| | | | Optimum condition | | |
| --- | --- | --- | --- | --- | --- |
| Enzyme | Main activity | Source | pH | Temperature (° C.) | Manufacture |
| Econase™ CE | cellulase | Trichoderma sp. | 4.0-5.5 | 55 | Novozymes A/S |
| Rapidase™ | pectinase, hemicellulase, cellulase | Aspergillus niger & Trichoderma longibrachiatum | 4.0-5.0 | 10-55 | DSM Food Specialties |
| Viscozyme™ | arabinase, cellulase, β-glucanase, hemicellulase, xylanase | Aspergillus sp. | 3.3-5.5 | 40-50 | Novozymes A/S |
| Celluclast™ 1.5L | cellulase | Trichoderma reesei | 4.5-6.0 | 50-60 | Novozymes A/S |
| Pectinex™ | pectinase | Aspergillus niger | 4.5 | 50 | Novozymes A/S |
| Rohament™ CL | cellulase | Trichoderma reesei | 4.5-5 | 50 | ABF Ingredients |
| Ultraflo™ L | β-glucanase | Humicola insolens | 6 | 40 | Novozymes A/S |
| Cytolase™ PCL 5 | pectinase | Asperigillus niger | 2.5-5.0 | 10-55 | DSM Food Specialties |
| Pectinase™ | pectinase | Aspergillus niger | 4.0-5.0 | 30-50 | Sigma Chemical |

Characteristics of Enzymes

Reagents and Test Animals

Sephadex™ G-100 used for purification of crude polysaccharide was available from GE Healthcare Co., Ltd. (Uppsala, Sweden) and dialysis tubing (MW cut-off 2,000) used for dialysis was available from Sigma (St. Louis, Mo., USA).

Standard materials, Pullulan series (P-800, 400, 200, 100, 50, 20, 10 and 5), used for measurement of molecular weight was available from Showa Denko Co., Ltd. (Tokyo, Japan).

RPMI 1640 medium, penicillin-streptomycin, fetal bovine serum and the like used for Mitogen and macrophage activity measurement tests were available from Gibco BRL (Grand Island Co, N.Y., USA) and CCK-8 (Cell counting Kit-8) available from Dojindo Molecular Technologies, Inc. (Kumamoto, Japan) was used for measuring cell proliferation capability.

A mouse IL-6 and IL-12 ELISA kit available from BD Biosciences Corp. (San Diego, Calif., USA) was used to measure cytokine. Lactate dehydrogenase (LDH) used for measuring cytotoxicity of NK cells to YAC-1 was a cytotoxicity colorimetric assay kit available from Oxford Biomedical Research (Oxford, Mich., USA). Rabbit anti-asialo GM1 (Wako, Osaka, Japan) was used to block functions of NK cells.

LPS (lipopolysaccharide from *Escherichia coli* 0127:B8) used as an immunoreactivity control group was obtained from Sigma Corp. PSK (polysaccharide-K from *Coriolus versicolor*) used herein was a soluble fraction obtained purifying Copolang™ available from Kwang Dong Pharmaceutical Co., Ltd. (Korea). Meanwhile, IgM-hemolysis sensitized sheep EA cells used for anticomplementary activity was obtained from Biotest K.K. (Tokyo, Japan) and anti-human C3 used for crossed immunoelectrophoresis was available from Sigma Corp. Other reagents used in this research were commercially available Grade No. 1 or higher products for assay.

In addition, 6-week old BALB/c and C57BL/6 mice, test animals used in this research were obtained from Nara biotech Co., Ltd. (Gyeonggi-do, Korea), adapted for one week and then used in the test. Breeding conditions were 23±3° C. and humidity of 60±10%, and animals were allowed free access to water and feed.

Statistical Treatment

The statistical treatment of test results was carried out by analyzing data using a statistical package for the social sciences (SPSS) program (SPSS Inc., Chicago, Ill. USA) and representing the same by mean±SD. Statistical significance in mean between respective groups was tested at a level of $\alpha<0.05$ using a Student's two-tailed t-test.

EXAMPLE 1

Preparation of Crude Polysacchride Fractions of Green Tea Hot-water Extracts and Enzymatic Hydrolysates and Immunoreactivity Thereof Preparation of Crude Polysacchride Fractions of Green Tea Hot-Water Extracts 20 g of green tea powder was suspended in 200 mL of DIW and hot-water extracted by heating at 100° C. until half of the original volume was obtained. The extract was centrifuged at 6,000 rpm for 20 minutes to remove residues, 95% ethanol of 4 times volume (v/v) was added to the extract, followed by stirring for 24 hours to precipitate polysacchride. The resulting precipitate was centrifuged at 7,000 rpm for 30 minutes, collected and was then dissolved in a small amount of distilled water, followed by dialysis using a dialysis tubing (MW cut-off 2,000) for 3 to 4 days and lyophilization (FreeZone 12 Liter, Labconco, Kansas City, Mo. USA) to obtain crude polysacchride fractions, GTW.

Preparation of Crude Polysacchride Fractions of Green Tea Enzymatic Hydrolysates Green tea powders were respectively treated with Econitase™ CE, Rapidase™, Viscozyme™, Celluclast™ 1.5L, Pectinex™, Rohament™, CL, UltrafloL™, Cytolase™ PCL 5 and Pectinase™ (added in an amount corresponding to 0.5% of green tea powder), the resulting enzymatic hydrolysates were centrifuged at 6,000 rpm for 20 minutes to remove residues, 95% ethanol of 4 times volume (v/v) was added thereto, followed by stirring for 24 hours to precipitate polysacchrides. The resulting precipitates were centrifuged at 7,000 rpm for 30 minutes, collected and dissolved in a small amount of distilled water, followed by dialysis using a dialysis tubing (MW cut-off 2,000) for 3 to 4 days and lyophilization to obtain crude polysacchride fractions treated with different enzymes (Table 2).

TABLE 2

| Enzymes | Crude polysacchride fractions |
|---|---|
| Hot-water extracts (non-treated control group) | GTW |
| Econitase ™ CE | GTW-0-E1 |
| Rapidase ™ | GTW-0-E2 |
| Viscozyme ™ | GTW-0-E3 |
| Celluclast ™ 1.5L | GTW-0-E4 |
| Pectinex ™ | GTW-0-E5 |
| Rohament ™ CL | GTW-0-E6 |
| UltrafloL ™ | GTW-0-E7 |
| Cytolase ™ PCL 5 | GTW-0-E8 |
| Pectinase ™ | GTW-0-E9 |

Naming crude polysaccharides obtained by hot-water extraction and treatment with respective enzymes

TEXT EXAMPLE 1

Evaluation of Immunoreactivity of Crude Polysacchride Fractions of Green Tea Hot-Water Extracts and Enzymatic Hydrolysates The immunoreactivity of GTWs, GTE-0-E1, GTE-0-E2, GTE-0-E3, GTE-0-E4, GTE-0-E5, GTE-0-E6, GTE-0-E7, GTE-0-E8 and GTE-0-E9, crude polysacchride fractions, was evaluated.

1-1 Anticomplementary Activity of Crude Polysacchride Fractions of Green Tea Hot-Water Extracts and Enzymatic Hydrolysates Preparation of Normal Human Serum (NHS)

Blood was collected from a healthy adult and allowed to stand at room temperature for about 15 minutes to induce coagulation, and the coagulated blood was crushed and allowed to stand at room temperature at about 5 minutes. The blood was allowed to stand at 4° C. for about 20 minutes and centrifuged at 3,000 rpm at 4° C. for 20 minutes, the separated serum was fractionated into 1 mL aliquots in micro centrifuge tubes, stored in a freezer at −70° C. and used in the test.

Anticomplementary Activity Test

Anticomplementary activity was measured using a complement fixation test method based on an erythrocytolysis level of the complement left in a sample after complement consumption of the sample using Meyer's method.

50 μL of each crude polysaccharide fraction sample of green tea hot-water extracts and enzymatic hydrolysates was mixed at a concentration of 1,000 μg/mL with GVB++ (Gelatin veronal buffer, pH 7.4, containing 0.1% gelatin, 0.15 mM Ca++ and 0.5 mM Mg++) and serum of normal human, followed by performing primary reaction at 37° C. for 30 minutes. 350 μL of GVB++ was added to the reaction, the mixture was continuously diluted 10 to 160 times, 750 μL, of GVB++ and 250 μL of IgM-sensitized sheep erythrocyte, EA cells, $1 \times 10^8$ cells/mL) were added thereto, followed by performing secondary reaction at 37° C. for 60 minutes, and 2.5 mL of phosphate buffered saline (PBS, pH 7.4) was added thereto to cease the reaction. The reaction solution was centrifuged at 2,000 rpm for 10 minutes, and residual hemolytic activity of the resulting supernatant was evaluated by measuring absorbance thereof at 412 nm. Anticomplementary activity was represented as an inhibition of 50% total complement hemolysis ($ITCH_{50}$, %) of a negative control group obtained by reaction with only serum of the normal human, GVB++ and distilled water. As a positive control group, PSK (polysaccharide-K), *Coriolus versicolor*-derived commercially available immune-booster was used for comparison.

On the basis that the activity of the negative control group is $ITCH_{SO}$ of 0%, activities of respective samples was measured. As a result, GTE-0-E2, GTE-0-0-E5, GTE-0-8 and GTE-0-E9 exhibited the highest activities, while crude polysaccharide, GTW, obtained by simple hot-water extraction exhibited the lowest activity (Table 3).

TABLE 3

| Crude polysaccharide fraction | Enzyme | Main activity | Anti-complementary activity ($ITCH_{50}$, %) |
|---|---|---|---|
| PSK (positive control) | — | — | 73.4 ± 3.2 |
| GTW | Non-enzymatic treatment | — | 43.2 ± 4.8 |
| GTE-0-E1 | Econase ™ CE | cellulase | 50.7 ± 3.6 |
| GTE-0-E2 | Rapidase ™ | pectinase, hemicellulase, cellulase | 65.8 ± 1.8 |
| GTE-0-E3 | Viscozyme ™ | arabinase, cellulase, β-glucanase, hemicellulase, xylanase | 49.1 ± 2.3 |
| GTE-0-E4 | Celluclast ™ 1.5L | cellulase | 58.6 ± 4.1 |
| GTE-0-E5 | Pectinex ™ | pectinase | 70.4 ± 2.5 |
| GTE-0-E6 | Rohament ™ CL | cellulase | 52.3 ± 3.1 |
| GTE-0-E7 | Ultraflo ™ L | β-glucanase | 54.2 ± 2.4 |
| GTE-0-E8 | Cytolase ™ PCL 5 | pectinase | 68.3 ± 2.9 |
| GTE-0-E9 | Pectinase ™ | pectinase | 77.4 ± 3.2 |

Anticomplementary activity of crude polysaccharide fractions of green tea hot-water extracts and hydrolysates (sample concentration; 1,000 μg/mL)

1-2 Induction Activity of Crude Polysacchride Fractions Upon IL-12 Production of Macrophages Preparation of Macrophage Culture Medium 1 mL of 3% thioglycollate medium (TG) was abdominally injected into BALB/c mice, the mice were sacrificed by dislocation of the cervical spine after 3 days, and 10 mL of a RPMI-1640 medium was injected into the abdomen to collect peritoneal exudate cells (PECs). The collected PECs were seeded on a 96 well culture plate at a concentration of $2.0 \times 10^6$ cells/well, incubated for 2 hours to adhere macrophages on the plate, and washed with a culture medium to remove unadhered cells. A sample was added to the macrophages such that the final concentration of the sample solution of crude polysaccharide fraction of green tea hot-water extracts and enzymatic hydrolysates was 200 μg/mL and incubated for 72 hours. After culturing, the culture medium was centrifuged at 1,500 rpm for 5 minutes, 150 μL of the cell culture supernatant was collected and the content of secreted cytokine, interleukin-12 (IL-12) was measured.

Measurement of Cytokine by Sandwich ELISA

The content of cytokine (IL-12) produced by macrophages was analyzed by sandwich ELISA (enzyme-linked immunosorbent assay). The capture antibody, monoclonal antibody specific to interleukin-12 was diluted with a coating buffer in accordance with manufacturer's instructions, the antibody dilution was fractionated into 100 μL of aliquots on a flat-bottomed 96-well microplate, and incubated at 4° C. for 12 hours. After completion of coating, the ELISA plate was washed with a washing buffer (PBS with 0.05% tween 20, PBST) three times, 200 μL of an assay diluent (PBS with 10% or 2% skimmed milk) was added thereto, followed by allowing to stand for one hour to block the surface of wells to which no antibody was adhered. After completion of blocking, respective wells were washed with washing buffer three times, and a recombinant mouse cytokine or macrophage culture medium, a continuously diluted standard material, was fractionated into 100 μL aliquots on the respective wells. The culture medium was reacted at room temperature for 2 hours, washed with a washing buffer, a detection antibody-biotin and enzyme reagent (avidin-horseradish peroxidase conjugate) was added thereto, followed by reacting at room temperature for one hour. After completion of reaction, the reaction solution was washed with a washing buffer 5 times, 100 μL of a substrate solution (tetramethylbenzidine, TMB) was added thereto, reacted with a cow for 30 to 60 minutes, and treated with 50 μL of a stop solution (1M $H_3PO_4$ or 2N $H_2SO_4$) to measure absorbance at 450 nm.

As a result, it was confirmed that GTE-0-E2, GTE-0-E5, GTE-0-E8 and GTE-0-E9 exhibited superior induction capability of IL-12 production in vitro (Table 4), and the same samples as in anticomplementary activity of Test Example <1-1> exhibited superior IL-12 production capability. The crude polysaccharide fractions of GTE-0-E2, GTE-0-E5, GTE-0-E8 and GTE-0-E9 are crude polysaccharide fractions obtained by treating pectinase with main active enzymes. The reason for this is considered that pectin present in green tea is severed by pectinase present in each enzyme, to produce an immunoactive component. Accordingly, GTE-0-E9 (Pectinase™, hydrolyzed crude polysaccharide) which exhibits the highest immunoactivity among pectinase-containing enzymatic hydrolysate fractions was subjected to the following test procedure and all of the GTE-0-E9 fractions are abbreviated as GTE-0.

TABLE 4

| Crude polysaccharide fraction | Enzyme | Main activity | IL-12 production activity (pg/mL) |
|---|---|---|---|
| LPS (positive control, | — | — | 687 ± 21 |

TABLE 4-continued

| Crude polysaccharide fraction | Enzyme | Main activity | IL-12 production activity (pg/mL) |
|---|---|---|---|
| 10 µg/mL) | | | |
| Saline | — | — | 48 ± 13 |
| GTW | Non-enzymatic treatment | — | 245 ± 19 |
| GTE-0-E1 | Econase™ CE | cellulase | 285 ± 14 |
| GTE-0-E2 | Rapidase™ | pectinase, hemicellulase, cellulase | 397 ± 24 |
| GTE-0-E3 | Viscozyme™ | arabinase, cellulase, β-glucanase, hemicellulase, xylanase | 230 ± 28 |
| GTE-0-E4 | Celluclast™ 1.5L | cellulase | 301 ± 13 |
| GTE-0-E5 | Pectinex™ | pectinase | 402 ± 17 |
| GTE-0-E6 | Rohament™ CL | cellulase | 298 ± 19 |
| GTE-0-E7 | Ultraflo™ L | β-glucanase | 299 ± 21 |
| GTE-0-E8 | Cytolase™ PCL 5 | pectinase | 412 ± 08 |
| GTE-0-E9 | Pectinase™ | pectinase | 465 ± 15 |

Induction of IL-12 production of macrophages by crude polysacchride fractions of green tea hot-water extracts and hydrolysates (sample concentration; 200 mg/mL)

TEXT EXAMPLE 2

Figure 2:
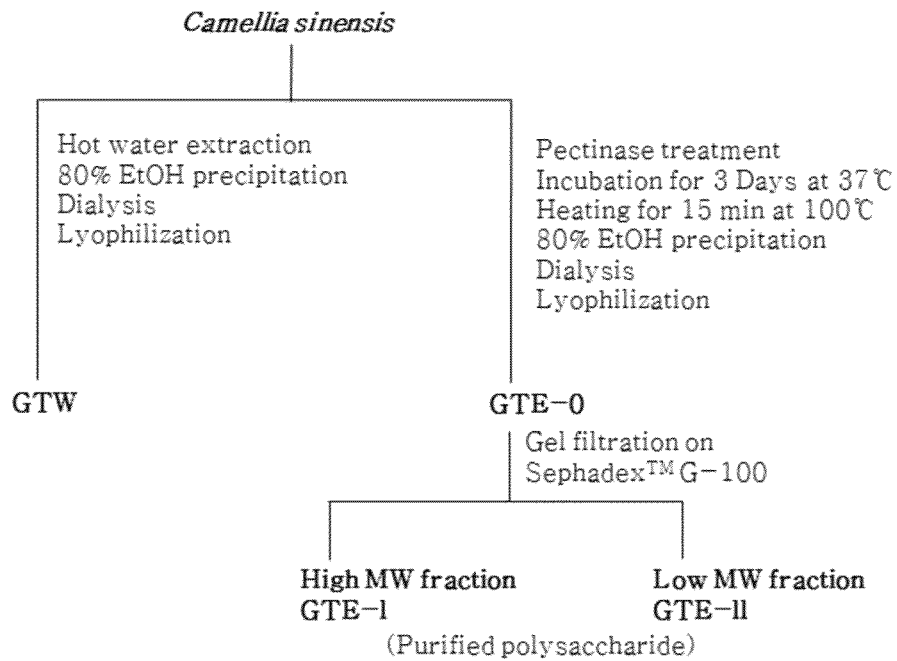
FIG. 2 shows a process for purification and separation of biologically active polysaccharides derived from green tea.
Figure 3:
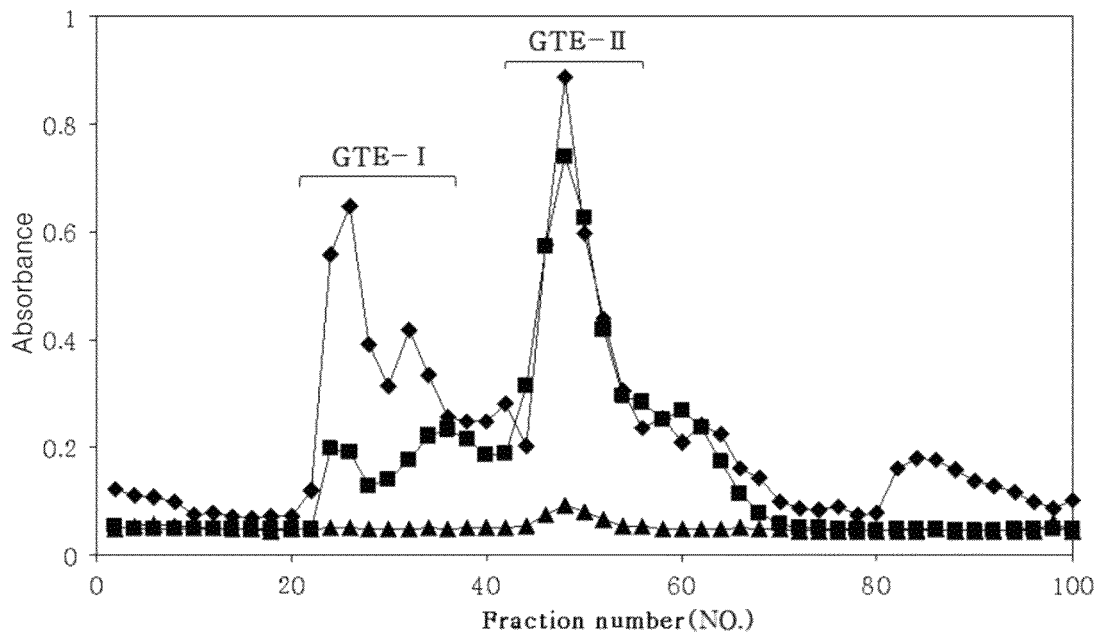
FIG. 3 shows results of gel permeation chromatography (GPC) of GTE-0-E9 separated from Pectinase™ hydrolysate of green tea using Sephadex™ G-100: Neutral sugar (490 nm); ■, Uronic acid (520 nm); and ▲, KDO (2-keto-3-deoxy-D-manno-octulosonic acid) (548 nm)

Separation and Purification of Polysaccharide from Green Tea 2-1 Separation and Purification of Polysacchride The crude polysaccharide, GTE-0, obtained by treating green tea with Pectinase™, which exhibited the most superior effects in Test Example 1 above, was dissolved in a small amount of distilled water, developed on a Sephadex™ G-100 column (4×120 cm) equilibrated with a 50 mM acetate buffer (pH 5.2) to perform GPC (Gel permeation chromatography). The eluate was fractionated into 6 mL of 100 aliquots, neutral sugar, acidic sugar, protein and KDO contents of the fractions were assayed to obtain an elution curve, and GTE-I and GTE-II, two fractions having different molecular weights and constituent components were separated. The fractions were subjected to concentration, dialysis and lyophilization to prepare a purified sample for analysis (FIGS. 2 and 3).

2-2 Assay of Constituent Components of Fractions

The content of neutral sugar in the polysaccharide sample was measured by a phenol-sulfuric acid method using galactose as a standard material. The content of acidic sugar was measured by an m-hydroxybiphenyl method using galacturonic acid as a standard. In addition, the content of TBA-positive material was measured by a thiobarbituric acid method using KDO as a standard material and the content of protein was quantitatively assayed by a Bradford method using bovine albumin as a standard material.

As a result of assay of constituent components of the fractions, it was confirmed that, GTW, crude polysaccharide simply obtained by hot-water extraction consisted of neutral sugar 54.3% and acidic sugar 45.7%, GTE-0 obtained by treating Pectinase™ consisted of neutral sugar 54.9% and acidic sugar 45.1%, and, GTE-I, the high-molecular weight fraction separated from GTE-0 consisted of neutral sugar 56.2% and acidic sugar 43.8%. These fractions exhibited similar chemical compositions. However, GTE-II, low-molecular weight fraction derived from GTE-0 contains KDO (specific monosaccharide) 2.2% as well as neutral sugar 54.2% and acidic sugar 43.6% (Table 5).

TABLE 5

| Chemical property | GTW | GTE-0 | GTE-I | GTE-II |
|---|---|---|---|---|
| Molecular weight (kDa) by HPSEC | — | — | 44 | 16 |
| Chemical composition | | | | (%) |
| Neutral sugar | 54.3 | 54.9 | 56.2 | 54.2 |
| Uronic acid | 45.7 | 45.1 | 43.8 | 43.6 |
| Protein | — | — | — | — |
| KDO | — | — | — | 2.2 |
| Componet sugar | | | | (Mole %) |
| 2-Me Fuc | 0.8 | 2.8 | — | 4.5 |
| Rha | 11.2 | 27.5 | 20.9 | 30.7 |
| Fuc | 0.8 | 3.7 | 2.9 | 4.2 |
| 2-Me Xyl | 3.6 | 2.3 | — | 3.7 |
| Ara | 38.7 | 30.2 | 29.2 | 29.0 |
| Xyl | 4.8 | 1.7 | 1.0 | 0.5 |
| Api | — | 1.0 | — | 2.1 |
| AceA | 0.4 | 1.3 | — | 2.6 |
| Man | 1.1 | 3.2 | 2.3 | 1.2 |
| Gal | 30.7 | 13.1 | 12.7 | 12.6 |
| Glc | 12.7 | 20.5 | 31.0 | 9.0 |

Figure 4:
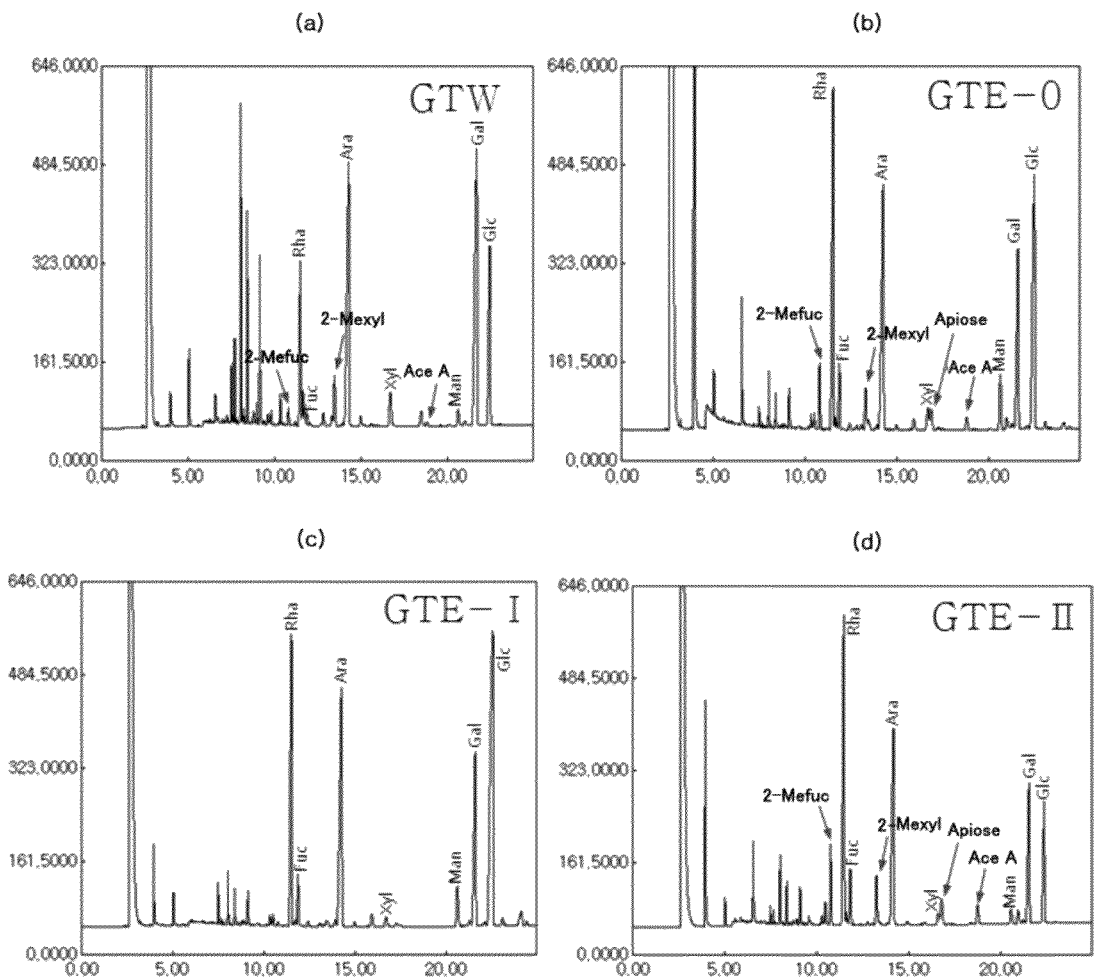
FIG. 4 shows GC chromatogram of polysaccharide fractions separated from green tea.

Green tea hot-water extracts, Pectinase™ hydrolysates and constituent components and constituent sugars of GTE-I and GTE-II separated therefrom As apparent from measurement results of constituent sugars, main constituent sugars of green tea crude polysaccharide were rhamnose (Rha), arabinose (Ara), galactose (Gal), and glucose (Glc). This behavior was similarly observed in both GTW, crude polysaccharide obtained by simple hot-water extraction and GTE-0, crude polysaccharide obtained by treating Pectinase™. However, there was remarkable difference in the composition of constituent sugars between GTE-I and GTE-II obtained by fractionating GTE-0. GTE-II contained specific sugars such as 2-methylfucose (2-Me-Fuc), 2-methylxylose (2-Me-Xyl), apiose (Api) and aceric acid (AceA) and a trace of KDO and DHA (3-deoxy-D-lyxo-2-heptulosaric acid) was also detected from GTE-II. On the other hand, these components were not observed in the high-molecular weight fraction, GTE-I (FIG. 4, Table 5). The 2-Me-Fuc, 2-Me-Xyl, AceA, DHA, KDO and the like detected from GTE-II were known as indicators of RG-II which constitutes pectin, green tea-derived GTE-I was considered to be polysaccharide of RG-I (rhamnogalacturonan I) and green tea-derived GTE-II was considered to be polysaccharide of RG-II (rhamnogalacturonan II).

2-2 Measurement of Molecular Weight of Purified Ppolysaccharide

In order to measure purification levels and molecular weights of purified fractions, green tea-derived polysaccharides, GTE-I and GTE-II, respective samples were dissolved at a concentration of 10 mg/mL in distilled water and were subjected to HPLC under analysis conditions shown in Table 6 using an Asahi-Pak GS-520+GS-320+GS-220 packed column.

Molecular weight was determined by obtaining retention times using Pullulan series (P-5, 10, 20, 50, 100, 200, 400 and 800) as standard materials, calculating Kav values with respect to respective molecular weights and performing conversion from a standard curve obtained therefrom.

TABLE 6

| | |
|---|---|
| Pump | SP-930D (YOUNG-LIN Co. Ltd. Anyang, Korea) |
| Detector | Refractive index (356-LC, Varian. Shropshire, UK) |
| Column | Asahi-Pak GS-520 + GS-320 + GS-220 packed column (Asahi Chemical Industry Co. Ltd. Tokyo, Japan) |
| Column size | 7.6 × 300 mm, each |
| Column temp. | 25° C. |
| Flow rate | 0.5 mL/min |
| Eluent | 50 mM ammonium formate buffer (pH 5.5) |
| Injection vol. | 20 μL |
| Integrator | Autochro data module (YOUNG-LIN Co. Ltd. Anyang, Korea) |

Figure 5:
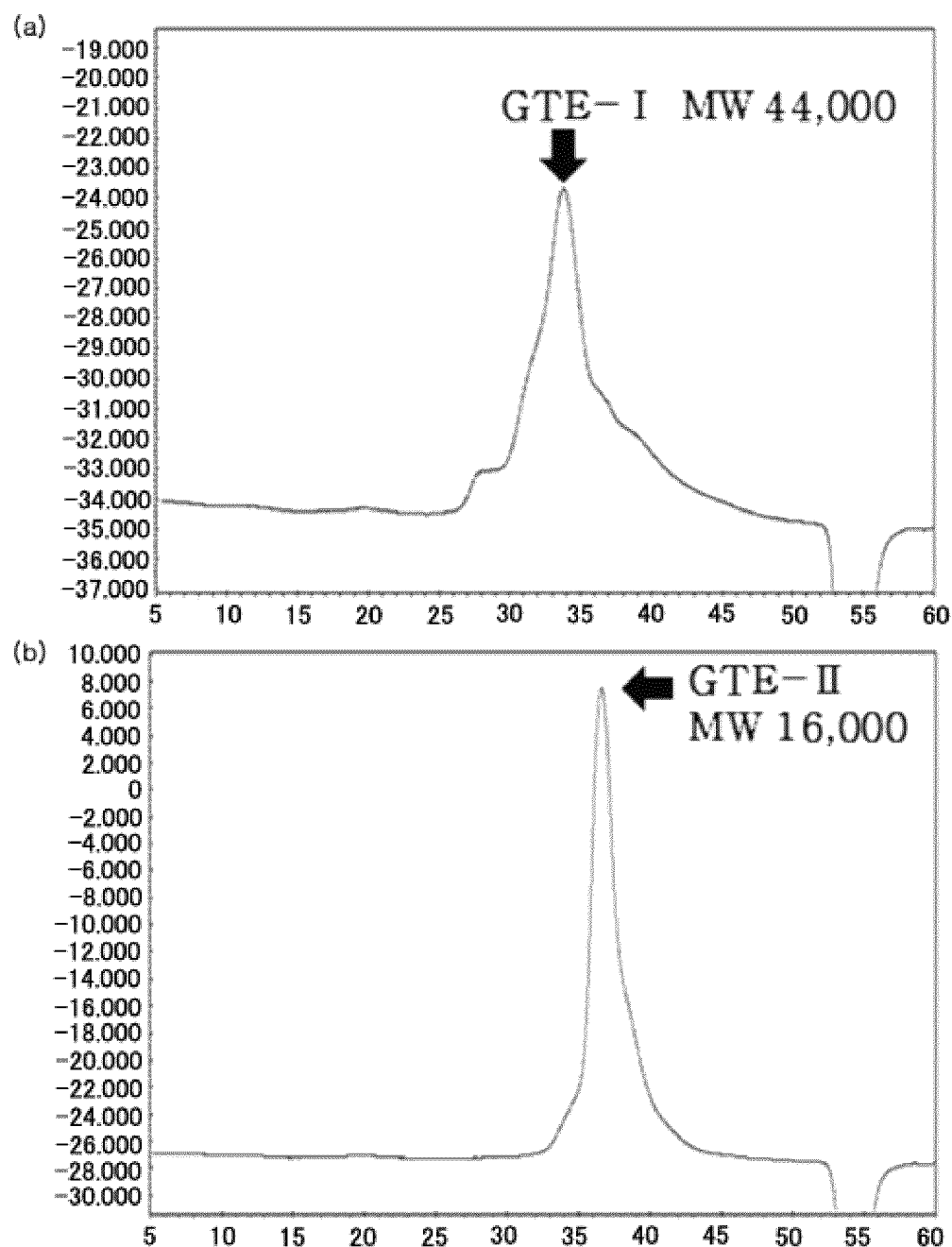
FIG. 5 shows elution patterns of high-performance size-exclusion chromatography (HPSEC) using an Asahi-Pak GS-520+GS-320+GS-220 column for GTE-I (a) and GTE-II (b) separated from crude polysacchride fractions of green tea Pectinase™ hydrolysate.

HPLC analysis conditions to confirm molecular weight and purification level of polysaccharides As a result, it was confirmed that GTE-I was about 44KDa polysaccharide and GTE-II was about 16 KDa polysacchride. From peak patterns, it was confirmed that GTE-II was bilaterally symmetrical, which means excellent purification level, while GTE-I was not observed as one peak and had no symmetric arrangement (FIG. 5). The reason for this is considered that side chains having many branches interfere with actions of Pectinase™ to prevent HG from being clearly decomposed, when Pectinase™ decomposes HG.

TEST EXAMPLE 3

Measurement of Immunoactivity of Green Tea-Derived Polysacchride 3-1 Anticomplementary Activity of Green Tea-Derived Polysacchride Preparation of Normal Human Serum (NHS)

Blood was collected from a healthy adult and allowed to stand at room temperature for about 15 minutes to induce coagulation of blood, and the coagulated blood was crushed and allowed to stand at room temperature for about 5 minutes. The blood was allowed to stand at 4° C. for about 20 minutes and centrifuged at 3,000 rpm at 4° C. for 20 minutes, and the separated serum was fractionated into 1 mL aliquots in micro centrifuge tubes, stored in a freezer at −70° C. and used in the test.

Anticomplementary Activity Test

Anticomplementary activity was measured using a complementary fixation test method based on an erythrocytolysis level of complement left in a sample after complement consumption of the sample using Meyer's method.

50 μL of each sample dissolved at various concentrations in distilled water was mixed with GVB++ (Gelatin veronal buffer, pH 7.4, containing 0.1% gelatin, 0.15 mM Ca++ and 0.5 mM Mg++) and normal human serum, followed by performing primary reaction at 37° C. for 30 minutes. 350 μL of GVB++ was added to the reaction, the mixture was continuously diluted 10 to 160 times, 750 μL of GVB++ and 250 μL of IgM-sensitizated sheep erythrocyte, EA cell, 1×10$^8$ cells/mL) were added thereto, followed by performing secondary reaction at 37° C. for 60 minutes, and 2.5 mL of phosphate buffered saline (PBS, pH 7.4) was added thereto to cease the reaction. The reaction solution was centrifuged at 2,000 rpm for 10 minutes, and residual hemolytic activity of the resulting supernatant was evaluated by measuring absorbance thereof at 412 nm. The anticomplementary activity was represented as an inhibition of 50% total complement hemolysis (ITCH$_{50}$, %) of a negative control group obtained by reaction only with serum of the normal human, GVB++ and distilled water. As a positive control group, PSK (polysaccharide-K), *Coriolus versicolor*-derived commercially available immune-booster was used for comparison.

Figure 6:
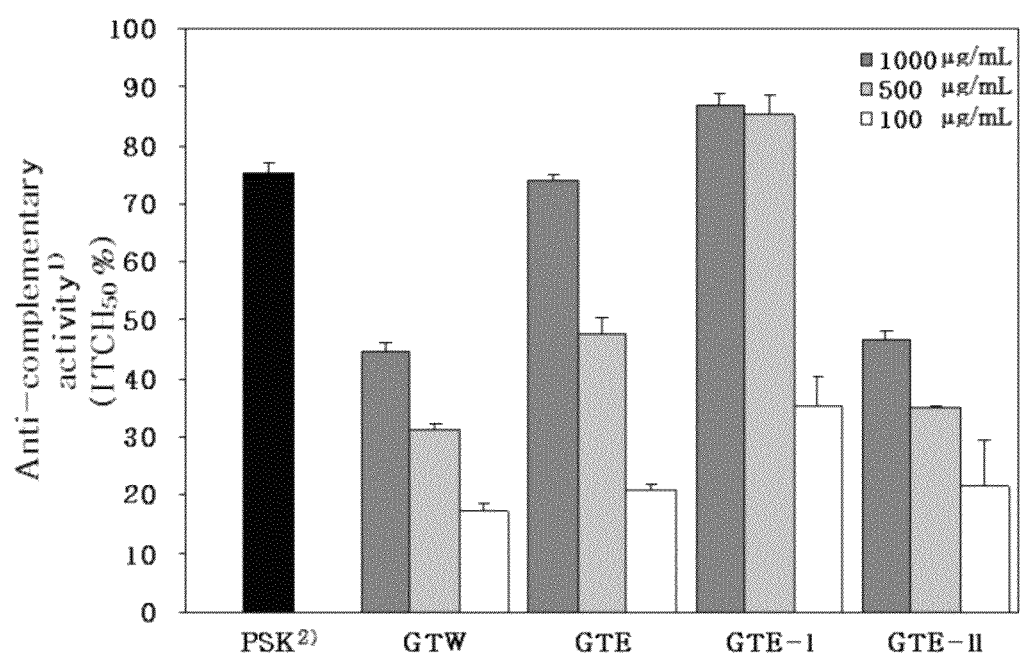
FIG. 6 shows anticomplementary activity of polysaccharides derived from green tea hydrolysates, 1) Anticomplementary activity is represented by $ITCH_{50}$ using Mayer's method and 2) PSK is used as a positive control group.

On the basis that the activity of a negative control group is an ITCH$_{50}$ of 0%, activities of respective samples were measured. As a result, GTE-0, the crude polysaccharide obtained by treating Pectinase™ exhibited superior anticomplementary activity as compared to GTW, crude polysaccharide obtained by simple hot-water extraction and exhibited similar concentration-dependent activity to the positive control group, commercially available immunoactive polysaccharide PSK. In addition, regarding GTE-I and GTE-II separated and purified from GTE-0, depending on molecular weight, GTE-I exhibited superior activity as compared to GTE-II and exhibited 87% higher activity at a concentration of 1,000 mg/mL than the positive control group (FIG. 6). Since, generally, polysaccharides which exhibit 60% or more anticomplementary activity at a concentration of 1,000 μg/mL are commonly considered to have pharmaceutical activity, GTE-0 and GTE-I fractions exhibit considerably superior complement system activation.

Analysis of Complement System Activity Pathway by 2-Dimensional Immunoelectrophoresis In order to confirm the activity pathway of a complement system, 2-dimensional immunoelectrophoresis was performed in accordance with a method of Morrison et al. A Mg++-EGTA-GVB-- buffer from which GVB++ buffer and Ca++ ions are selectively removed, and an EDTA-GVB-- buffer from which both Ca++ and Mg++ ions are removed were prepared and mixed with a sample and NHS, followed by reacting at 37° C. for 30 minutes and cooling. The reaction solution was dissolved in a barbital buffer (pH 8.6), 5 μL of the resulting solution was loaded on 1% agarose gel plate (5×5 cm) wells, and primary electrophoresis (75 mA/plate) was performed at 4° C. for about 3 hours. Then, secondary electrophoresis (25 mA/plate) was performed on a 1% anti-human C3-containing agarose gel plate at 4° C. for about 15 hours. The developed gel was dyed with bromophenol blue for about 10 minutes, decolorized, and activation of C3 was observed by confirming precipitation lines.

Figure 7:
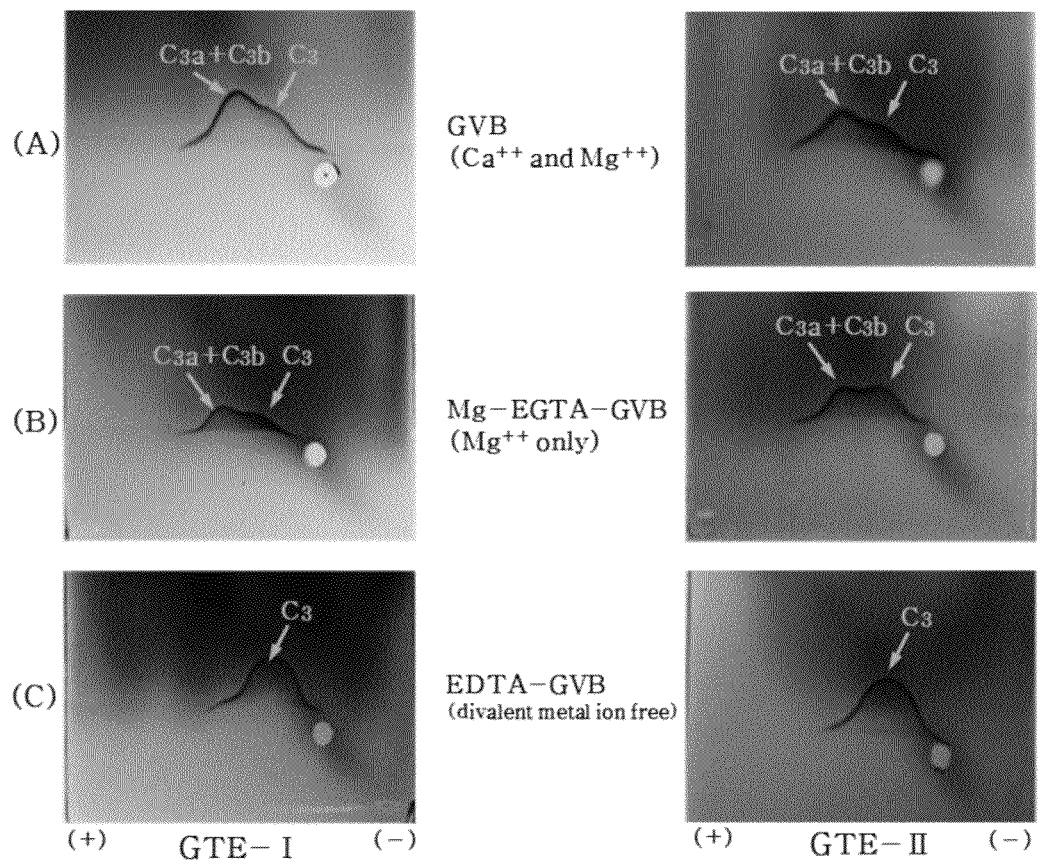
FIG. 7 shows crossed immunoelectrophoresis patterns in which C3 was converted by GTE-I and GTE-II in the presence of Ca ions. Normal human serum was incubated together with samples of GVB++ (A), MG++-EGTA-GVB-- (B) and EDTA-GVB--(C) at 37° C. for 30 minutes. The serum was subjected to immunoelectrophoresis using an anti-human C3 antibody and thus transferred to a C3-cut product.

As a result, in a case where GTE-I and GTE-II react with normal human serum in an EDTA-GVB-- reaction system from which bivalent metal ions have been removed, activation of C3 was not performed and only one precipitation line was thus observed, while two precipitation lines were observed in a GVB++ reaction system in which both Ca++ and Mg++ are present, and in a Mg++-EDTA-GVB-- in which only Mg++ ions are selectively added. In particular, the second peaks from wells in the Mg++-EDTA-GVB-- reaction system of GTE-I were smaller than those of the GVB++ reaction system. It can be seen that alternative pathway activation is relatively low when taking into consideration the fact that the first peak from wells was a precipitation line derived from C3 and the second peak therefrom was a precipitation line derived from C3a and C3b and that GTE-II exhibits similar activation capabilities (FIG. 7). From the results above, it can be seen that GTE-I and GTE-II obtained by fractionating, GTE-0, crude polysaccharide obtained by treating green tea with Pectinase™, can activate a complement system in accordance with a classical pathway and an alternative pathway.

3-2 Toxicity of Green Tea-Derived Polysaccharide in Macrophages

In order to confirm cytotoxicity of samples in normal cells, PBS was used and a polysaccharide sample solution prepared at a concentration of 2 mg/mL was continuously 2 5 diluted at 4 times with an RPMI 1640 medium such that the concentration was adjusted to 1 mg/mL to 0.06 µg/mL, and the dilution was fractioned into 100 µL aliquots onto a flat-bottomed 96-well microplate (Nunc™, Roskilde, Denmark). 100 µL of macrophages ($2 \times 10^5$ cells/mL of RPMI 1640 medium) induced for 72 hours by injecting 1 mL of 3% TG (thioglycollate medium) into 6-week old female BALB/C mice were added thereto and incubated at 37° C. in a 5% $CO_2$ incubator for 72 hours. The effects of cytotoxicity depending on concentration of the sample were evaluated by diluting 5 times the sample with CCK-8, adding 50 µL of diluant to each well, reacting at 37° C. in a 5% $CO_2$ incubator for 30 to 60 minutes and measuring absorbance at 450 nm.

Figure 8:
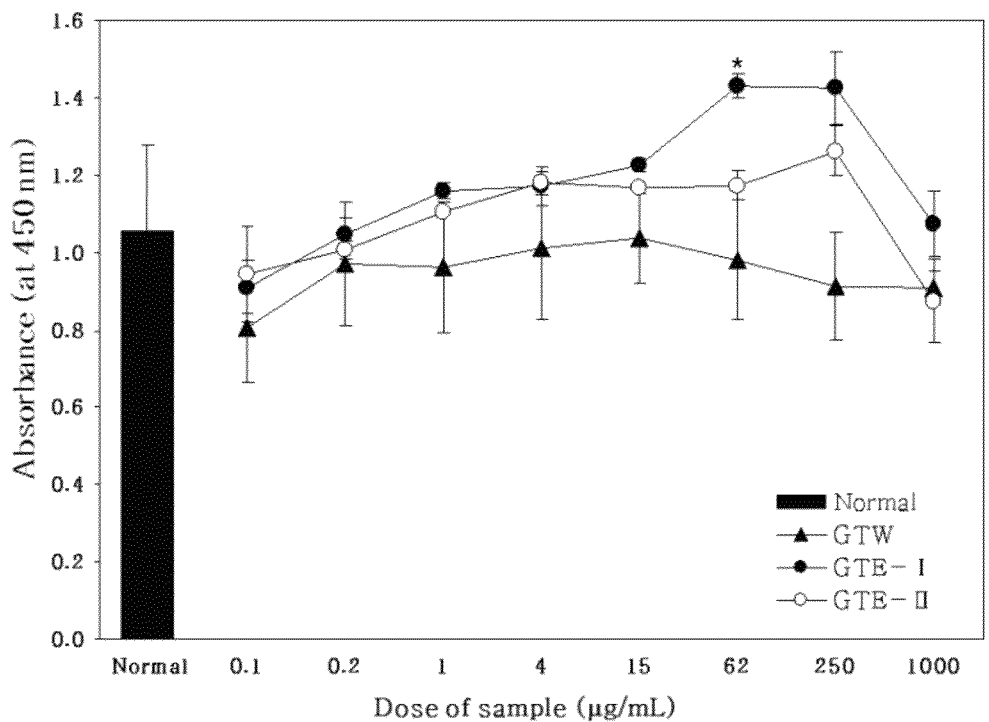
FIG. 8 shows results of in vitro cytotoxicity of green tea-derived GTW, GTE-I and GTE-II to mouse peritoneum macrophages.

As a result, cytotoxicity of cells was not observed in all green tea polyschride sample groups regardless of concentration. However, GTE-I-treated group exhibited proliferation of macrophages at a concentration of 62 to 250 µg/mL (FIG. 8). This behavior indicates that the polysaccharide fraction obtained by treatment of Pectinase™ reduces toxicity and induces cell proliferation, that is, mitogen efficacy, rather than a polysaccharide fraction obtained by simple hot-water extraction.

3-3 Measurement of Lymphocyte Proliferation Activity of Green Tea-Derived Polysacchride 6 week old female BALB/c mice were sacrificed by dislocation of the cervical spine, and the spleen was aseptically extracted, crushed (100 mesh) in PBS using a stainless steel mesh and filtered (200 mesh) to obtain lymphocyte cells. 5 mL of 0.2% NaCl was added to the cells for 15 to 30 seconds, the mixed erythrocytes were destroyed by shaking, the cells were washed with an RPMI 1640 medium 2 to 3 times, and the number of cells was adjusted to $5 \times 10^6$ cells/mL using a hemacytometer. The number of living lymphocyte cells was counted after the cells were dyed with 0.2% trypan blue (Gibco BRL Co, Ltd.). 180 µL of the separated spleen lymphocyte cells and 20 µL of sample dissolved in PBS were seeded on a flat-bottomed 96-well microplate such that the total volume was adjusted to 200 µL and incubated at 37° C. in a 5% $CO_2$ incubator for 72 hours. At this time, for positive control of B-lymphocyte and T-lymphocyte proliferation, LPS and concanavalin A were used in a final concentration of 10 µg/mL. The lymphocyte-stimulating activity of each material was evaluated by measuring absorbance at 450 nm in accordance with the manufacturer's instructions using a CCK-8 kit utilizing a water soluble tetrazolium salt (WST).

Figure 9:
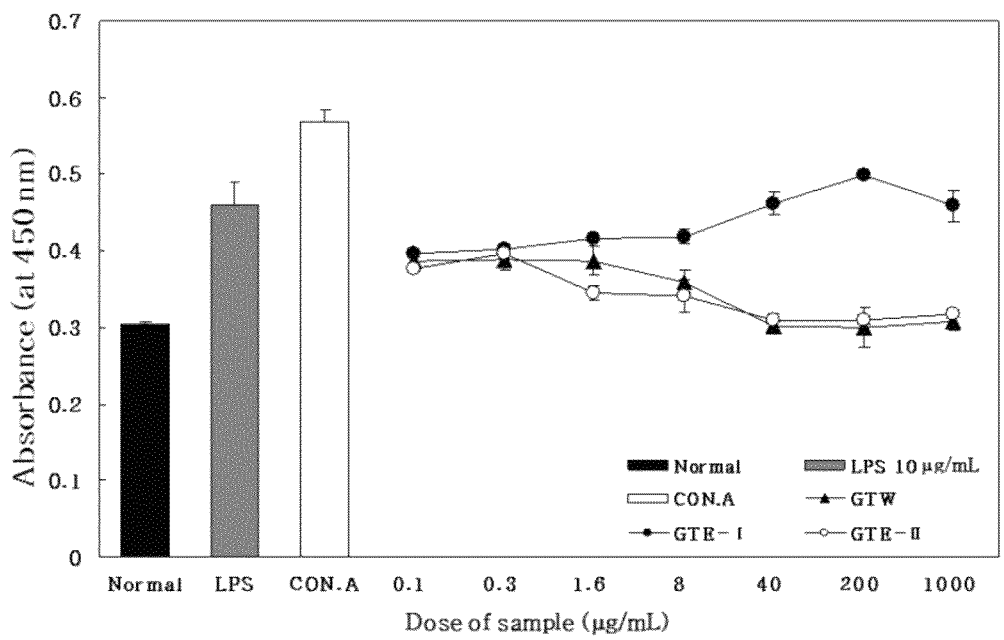
FIG. 9 shows in vitro lymphocyte proliferation activity of green tea-derived GTW, GTE-I and GTE-II.

The immune-stimulating activity of green tea-derived polysaccharide fractions was investigated through spleen cell proliferation effects. As a result, it can be seen that all sample treatment groups exhibited superior proliferation activities, as compared to test groups of spleen cells not treated with a sample and GTE-I exhibited remarkably superior activity, as compared to other polysaccharide fractions. In particular, GTE-I exhibited the highest proliferation activity at a concentration of 200 µg/mL (FIG. 9). This behavior demonstrates that a method for preparing polysaccharide samples by treatment with Pectinase™ can increase immunoreactivity of samples, as compared to a method for preparing polysaccharide samples from green tea by hot-water extraction. More detailed tests associated with activation of immune cells by respective fractions were performed.

3-4 Measurement of Induction Activity of Cytokine Production of Macrophage by Green Tea-Derived Polysacchride Preparation of Macrophage Culture Medium 1 mL of 3% TG was abdominally injected into BALB/c mice, after 3 days, the mice were sacrificed by dislocation of the cervical spine, and 10 mL of an RPMI-1640 medium was injected into the abdomen to collect peritoneal exudative cells (PEC). The collected PECs were seeded on a 96 well culture plate at a concentration of $2.0 \times 10^6$ cells/well, incubated for 2 hours to adhere macrophages to the plate, and washed with a culture medium to remove un-adhered cells. A sample was added to macrophages such that the final concentration of the polysaccharide sample solution was 0.06 to 1 mg/mL and incubated for 72 hours. After culturing, the culture medium was centrifuged at 1,500 rpm for 5 minutes, 150 µL of the cell medium culture supernatant was collected and the content of IL-12 and IL-6, cytokines induction-secreted by the incubated supernatant, was measured.

Measurement of Cytokine by Sandwich ELISA

The content of cytokine produced by macrophage was analyzed by sandwich ELISA (enzyme-linked immunosorbent assay). The capture antibody, a monoclonal antibody specific to interleukin-12 was diluted with a coating buffer in accordance with the manufacturer's instructions, and the diluted solution was fractionated into 100 µL aliquots on a flat-bottomed 96-well microplate and incubated at 37° C. for 12 hours. After completion of coating, the ELISA plate was washed with a washing buffer (PBS with 0.05% tween 20, PBST) three times, 200 µL of an assay diluent (PBS with 10% or 2% skim milk) was added thereto, followed by allowing to stand for one hour to block the surface of wells to which no antibody was adhered. After completion of blocking, respective wells were washed with washing buffer three times, a recombinant mouse cytokine or macrophage culture medium, a continuously diluted standard material was fractioned into 100 µL aliquots on the wells. The culture medium was reacted at room temperature for 2 hours and washed with a washing buffer and a detection antibody-biotin and enzyme reagent (avidin-horseradish peroxidase conjugate) was added thereto, followed by reaction at room temperature for one hour. After completion of reaction, the reaction solution was washed with a washing buffer 5 times, 100 µL of a substrate solution (tetramethylbenzidine, TMB) was added thereto, reacted with a cow for 30 to 60 minutes, and treated with 50 µL of a stop solution (1M $H_3PO_4$ or 2N $H_2SO_4$) to measure absorbance at 450 nm.

Figure 10:
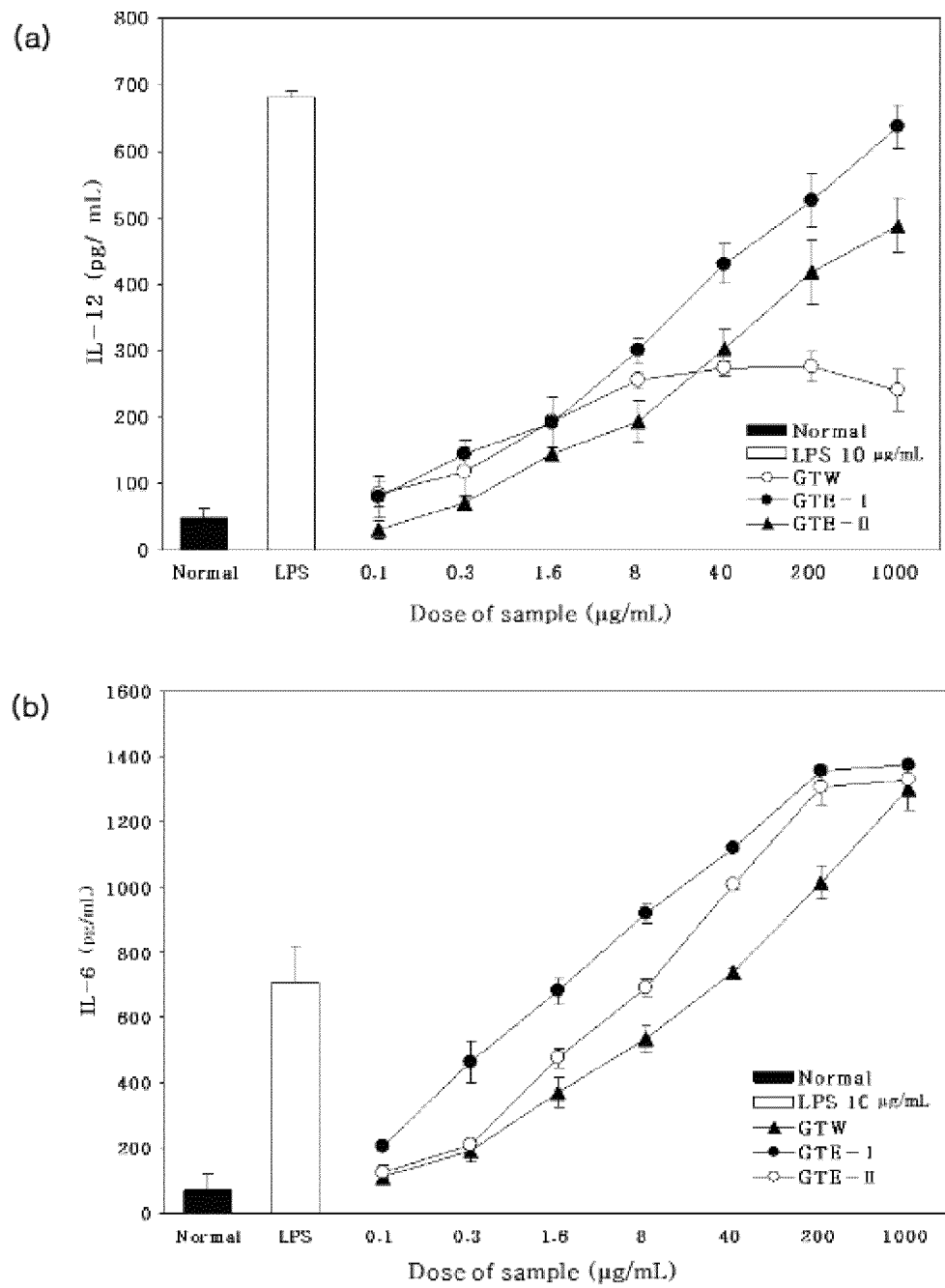
FIG. 10 shows in vitro effects of green tea-derived GTW, GTE-I and GTE-II upon cytokine produced by mouse peritoneum macrophages.

As a result, production of cytokine in IL-6 increases, as the concentration thereof increases. In all sample groups at a concentration of 40 µg/mL, cytokine was produced in an amount equivalent to the positive control group, LPS. In particular, at a constant concentration, GTE-I and GTE-II can produce a higher amount of cytokine than GTW (FIG. 10 (*b*)). Also, IL-12 exhibited similar behaviors to IL-6. That is, IL-12 exhibited an increase in cytokine production, as the concentration thereof increased. In particular, at a constant concentration, GTE-I and GTE-II exhibited superior cytokine production than GTW (FIG. 10(*a*)). These two results of cytokine-induction capability ascertained that enzymatic hydrolysate polysaccharides of GTE-II and GTE-I exhibit an increase in cytokine production capability in this order, as compared to GTW, crude polysaccharide obtained by simple hot-water extraction, and enzyme treatment is thus useful for separating a major activity component which activates immune cells from the overall polysaccharide of green tea. In addition, it is considered that green tea mature leaf-derived polysaccharide stimulates macrophages and thus positively affects biophylaxis during the initial stage of immune reaction.

Activation of Green Tea-Derived Polysaccharide Upon Cancer Cell Lysis of Natural Killer Cells (NK Cell Activity)

The cell-killing capability (cytotoxicity, lysis) of NK cells to infected cells and cancer cells is improved by secretion of cytokines such as interleukin, other operative cells, that is, Tc lymphocytes (cytotoxic T cells; CTL) induce activation of macrophages. Accordingly, the effect of stimulating NK cell activity causes an increase in innate immunity as well as potentiality of simple anticancer effects.

The polysaccharide sample purified from green tea was intravascularly injected at a dose of 1 μg/mouse, 100 μg/mouse and 1,000 μg/mouse into 6-week old female BALB/c mice, the mice were sacrificed by dislocation of the cervical spine after 3 days of the injection, and the spleen was aseptically extracted, crushed (100 mesh) in PBS using a stainless steel mesh and filtered (200 mesh) to obtain lymphocyte cells. 5 mL of 0.2% NaCl was added to the cells for 15 to 30 seconds, the mixed erythrocytes were destroyed by shaking, the cells were washed with a no-serum medium 3 times, and the number of cells was adjusted to $1 \times 10^6$ cells/mL using a hemacytometer. The cells were used as effector cells. YAC-1 lymphoma cells highly sensitive to mouse NK cells as target cells were added to a round-bottomed 96-well microplate (Becton Dickinson Labware, Franklin Lakes, N.J., USA) such that a ratio of effector cells to target cells (E/T ratio) was adjusted to 25, 50 and 100, incubated at 37° C. in a 5% $CO_2$ incubator for 18 to 24 hours, and centrifuged at 1,500 rpm for 5 minutes to collect 100 μL of a cell culture medium supernatant. Cytotoxicity of NK cells was evaluated by measuring LDH which was killed by effector cells, NK cells, and separated from the target cells into the culture supernatant using an LDH assay kit. The tumor cell-killing capability (cytotoxicity, lysis) of NK cells was calculated by the following equation (Equation 1).

$$\text{Lysis (\%)} = \frac{E - S}{M - TSR} \times 100 \quad \langle \text{Equation 1} \rangle$$

Figure 11:
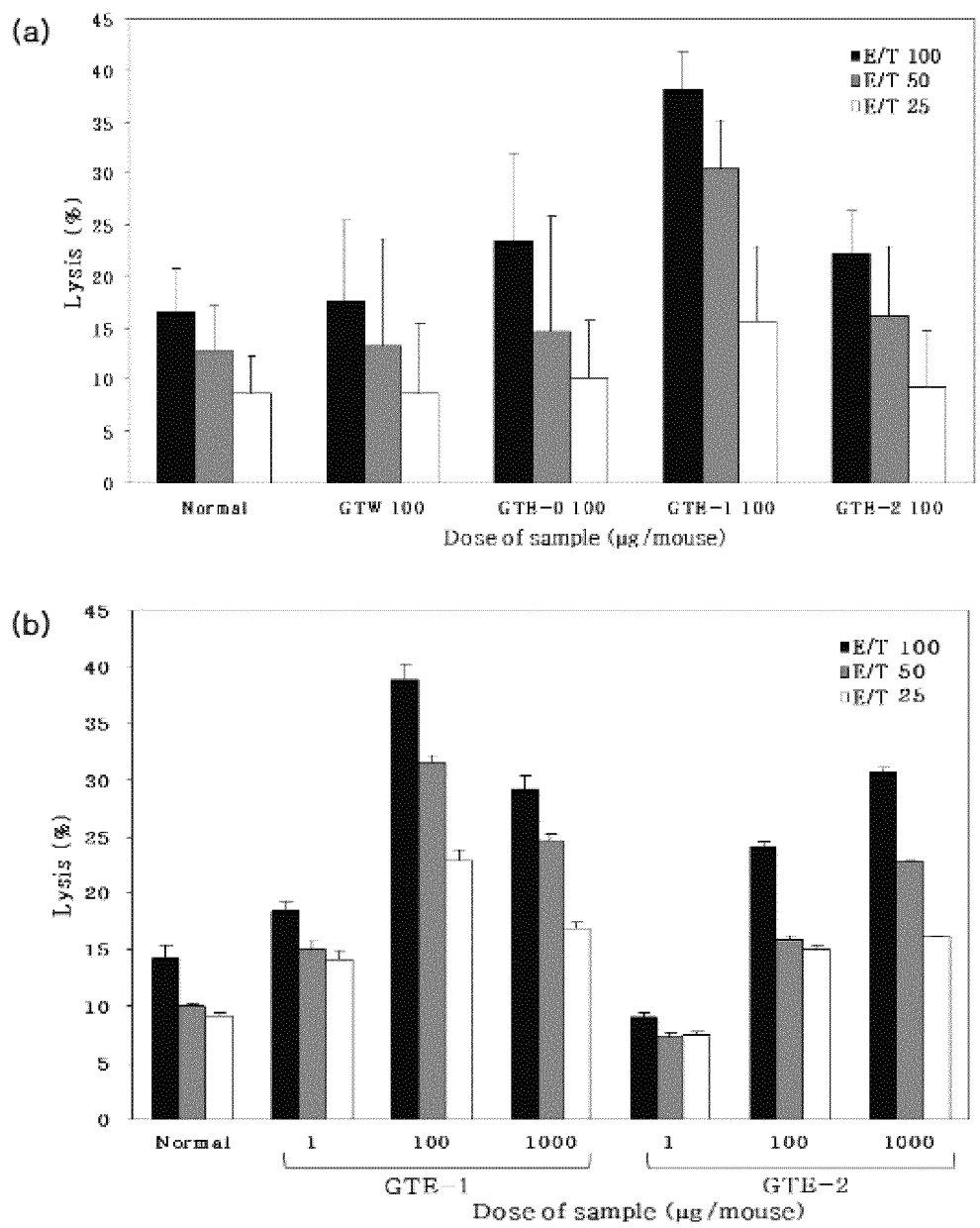
FIG. 11 shows ex vivo effects of green tea-derived GTW, GTE-I and GTE-II upon toxicity of NK cells to cancer cells.

E—experimental release rom effector cell,
S—average spontaneous release from target cell,
M—maximum release from target cell,
TSR—spontaneous release from target cell As a result of measurement of NK cell-stimulating activity through administration of a sample, as compared to NK cytotoxicity of a normal mouse, groups to which GTE-I or GTE-II is administered exhibited an increase in cytotoxicity to tumor cell from low concentration to high concentration depending on concentration. GTE-I exhibited the highest activity at a concentration of 100 μg/mouse and GTE-II the highest activity at a concentration of 1,000 μg/mouse. Accordingly, in terms of activation of NK-cells, GTE-I exhibited higher activity than GTE-II (FIG. 11 (a) and (b)).

TEST EXAMPLE 4

Anticancer Activity of Green Tea-Derived Polysaccharide 4-1 Antimetastatic activity of green tea-derived polysaccharide The antimetastatic activity of samples was measured using a simulated animal tumor metastatic model using highly proliferative lung carcinoma cell lines, B16BL6. In order to observe the tumor proliferation effects of samples, the number of B16BL6 melanoma cells was adjusted to $4 \times 10^4$ cells/mouse, the B16BL6 melanoma cells were intravenously injected into 6-week old female C57BL/6 mice, and the sample was intravenously injected at different concentrations 2 days before tumor administration. 14 days after tumor administration, the mice were sacrificed by dislocation of the cervical spine, the lungs, the target organ of tumor cells were extracted and metastasized tumors were fixed and dyed in Bouin's solution (Sigma) and metastasized black tumor colonies were counted. The effects of antitumor metastasis by the sample were evaluated by comparison with a control group into which only tumor was injected.

Figure 12:
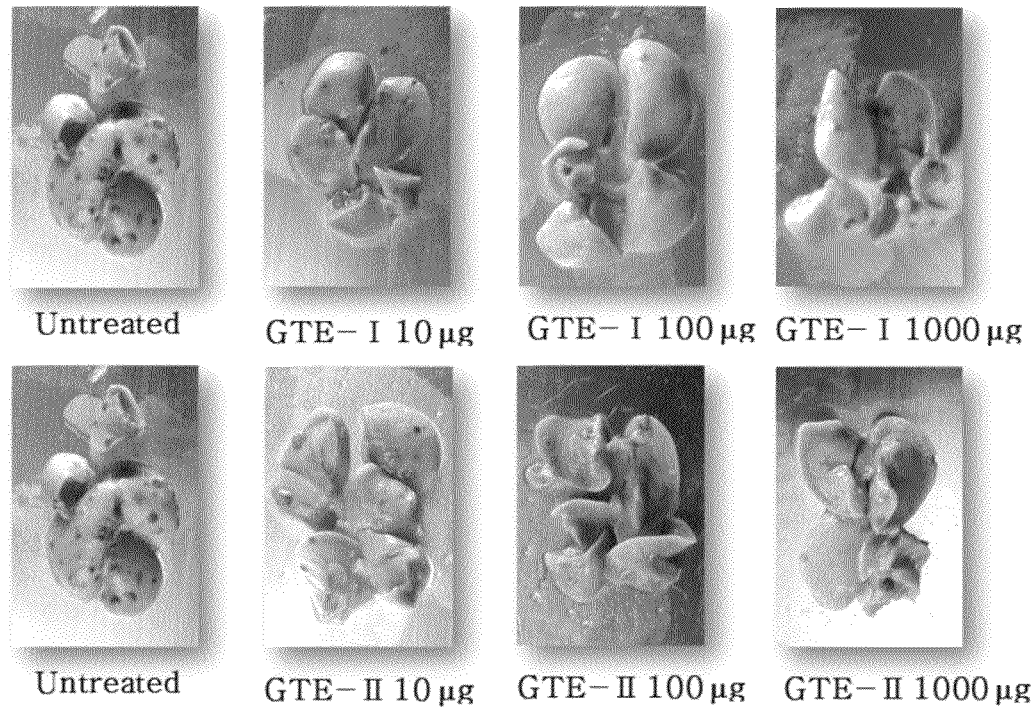
FIG. 12 is an image showing inhibitory activity of green tea-derived GTW, GTE-I and GTE-II in a lung proliferation model induced by intravenously injecting B16BL6 tumor cells.

As a result of test results, an average of 70 colonies was counted in the tumor control group. Inhibition of GTE-I and GTE-II was calculated, based on the colony number. As a result, it can be seen that all test groups to which the sample was administered exhibited a high inhibition rate of 75% or more. In addition, it can be seen that GTE-I and GTE-II exhibited an increase in inhibition depending on concentration from low concentration to high concentration. GTE-I exhibited the highest inhibitory activity of 93% at a concentration of 100 μg/mouse and GTE-II exhibited the highest inhibitory activity of 94.3% at a concentration of 1,000 μg/mouse. This behavior is the same as tumor cell-killing capability (cytotoxicity) of NK cells (Table 7 and FIG. 12) as shown in tests above. In the simulated metastatic model, the antitumor activity through administration of BRM material is well-known to be mainly related to activation of macrophages or NK cells. Accordingly, hereinafter, in order to confirm whether the mechanism of antitumor activity by the sample in <4-2> is due to activation of NK cells, antitumor activity of mice in which the function of NK cells is artificially removed, was investigated.

TABLE 7

| | Number of Cancer colony | | | | | |
|---|---|---|---|---|---|---|
| | GTE-I | | | GTE-II | | |
| Dose (μg/mouse) | Mean ± SD | Range | Inhibition % | Mean ± SD | Range | Inhibition % |
| Untreated | 69.8 ± 2.1 | 68~72 | 0 | 69.8 ± 2.1 | 68~72 | 0 |
| 10 μg | 17.3 ± 2.1 | 15~19 | 75.3 | 15.5 ± 9.6 | 15~16 | 77.8 |
| 100 μg | 4.5 ± 1.3 | 3~6 | 93.6 | 5.3 ± 1.0 | 4~6 | 92.5 |
| 1000 μg | 25.3 ± 3.3 | 22~29 | 63.9 | 4.0 ± 1.6 | 2~6 | 94.3 |

Antimetastatic activity of green tea leaf-derived GTE-I and GTE-II in lung metastatic model induced by intravenous injection of B16BL6 tumor cells 4-2 Antimetastatic Activity of Green Tea Leaf-Derived Polysaccharide in NK Cell Function-Removed Mice In order to measure antimetastatic activity of samples in NK cell function-removed mice, on one day before the sample was inoculated, 50 μL of anti-asialo GM1 was abdominally injected into mice to remove NK cell functions thereof. The number of B16BL6 lung carcinoma cells was adjusted to 4×10⁴ cells/mouse, the B16BL6 lung carcinoma cells were intravenously injected into 6 week old female C57BL/6 mice and the sample was intravenously injected at different concentrations 2 days before carcinoma administration. 14 days after carcinoma administration, the lungs, the target organ of carcinoma cells was extracted and antimetastasis effects of the sample were measured.

Figure 13:
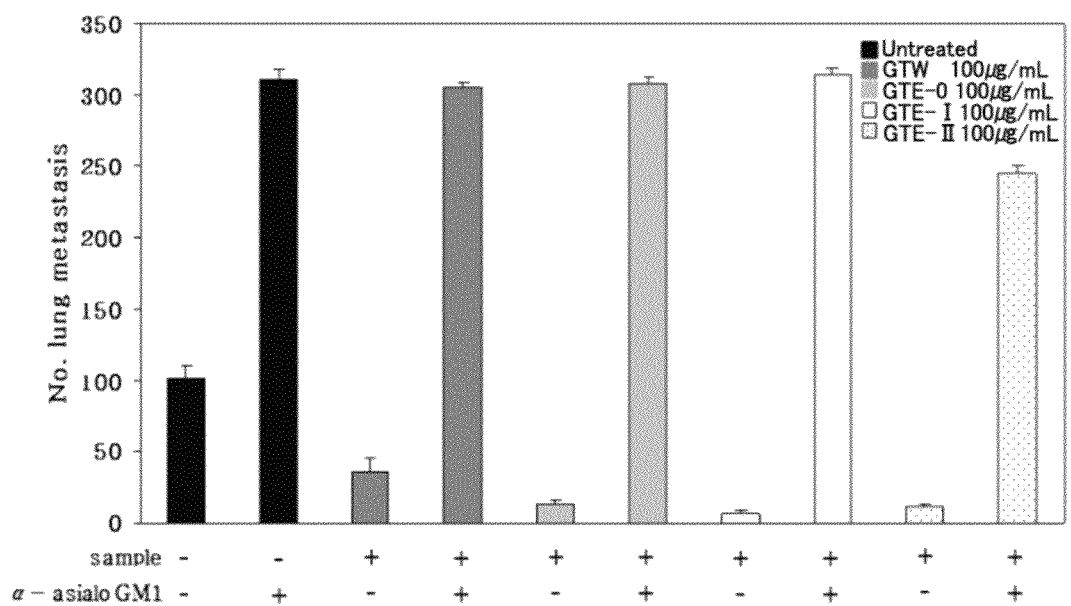
FIG. 13 shows in vivo effects of green tea-derived GTW, GTE-I and GTE-II upon removal of NK cell function associated with antimetastatic activity. A rabbit anti-asialo GM1 serum was injected into mice in order to eliminate NK cell function 3 days before B16BL6 tumor cells were inoculated thereto, a sample (100 μg/mouse) was administered thereto 2 days before inoculation of the tumor cells, a tumor was inoculated and the mice were sacrificed for evaluation after 14 days.
Figure 14:
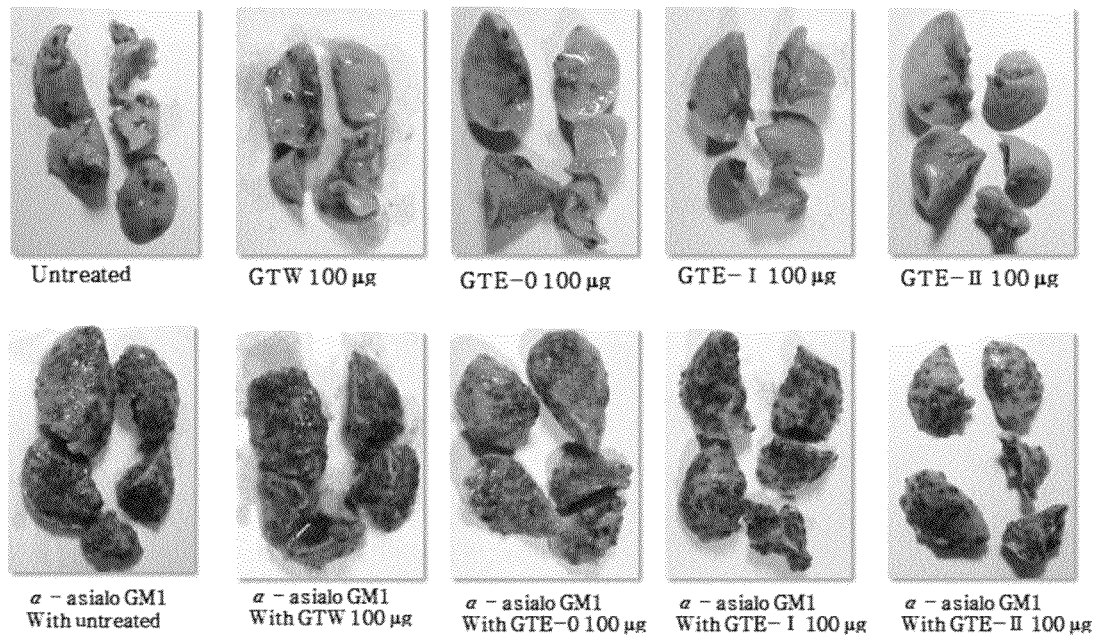
FIG. 14 is an image showing effects of green tea-derived polysaccharides on removal of NK cell function of antimetastatic activity.

As a result, a tumor control group to which only tumor cells were administered had metastasized colony number of 100 on average, while a test group in which NK cells were blocked using a rabbit anti-asialo-GM1 antibody had an increased colony number of 310. This indicates that NK cells play an important role in anti-metastasis effects in normal mice. In addition, the colony numbers of test groups to which GTW, GTE-0, GTE-I and GTE-II were administered at a concentration of 100 μg/mouse were 35, 13, 7 and 10, which means a high inhibition rate of 65% or more. However, GTE-II administered at a concentration of 100 μg/mouse to NK cell function-removed mice exhibited low inhibition of 21%, and GTW, GTE-0 and GTE-I did not exhibited inhibitory activity (FIGS. 13 and 14). These results demonstrate that antimetastasis activities of GTW, GTE-0 and GTE-I entirely depend on NK cell and GTE-II mediates NK cells as well as other immune stimulating activities.

4-3 Activity and Cytotoxicity of Macrophages to Cancer Cells

Evaluation of Activity of Macrophages by Green Tea-Derived Polysaccharide

Macrophages (4×10⁵ cells/mL of RPMI 1640 medium) induced for 72 hours by injecting 1 mL of 3% TG into 6-week old female Balb/c mice were seeded onto a slide glass and incubated for 30 minutes at 37° C. in a 5% $CO_2$ incubator. Non-adhered cells were removed by washing with PBS, 100 μg/mL of GTW, GTE-0, GTE-I and GTE-II samples were prepared and added thereto, incubated at 37° C. in a 5% $CO_2$ incubator for 48 hours. The slide glass was washed with PBS, immobilized in Bouin's solution (Sigma) for 5 minutes, dyed by Giemsa dying for 2 hours, dehydrated with acetone and sealed with Entelan. The number of activated macrophages was counted at 4 points by a microscope (400×) to obtain an average and standard deviation.

Figure 15:
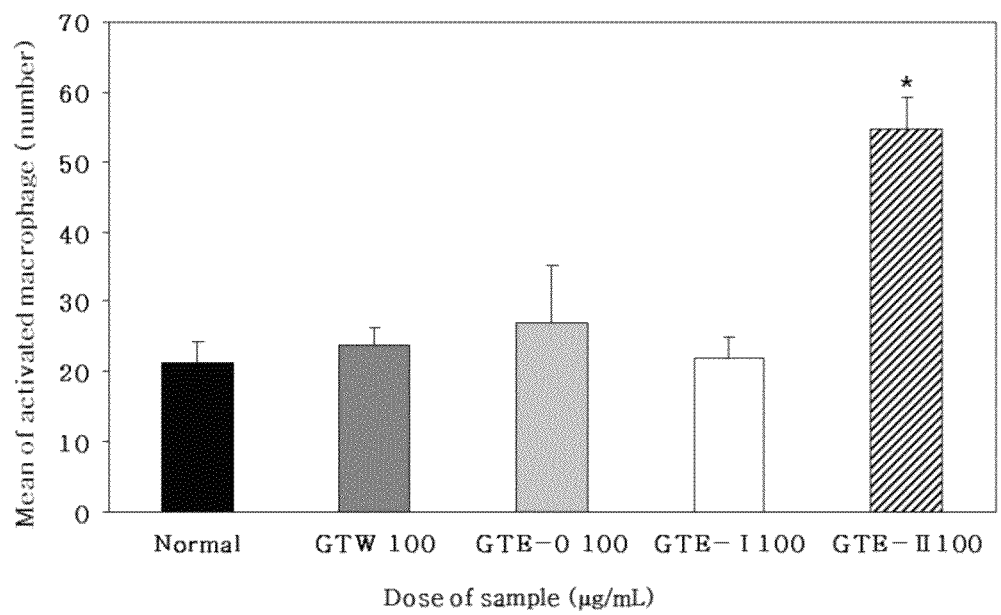
FIG. 15 shows effects of green tea-derived GTW, GTE-I and GTE-II on activity of mouse macrophages.
Figure 16:
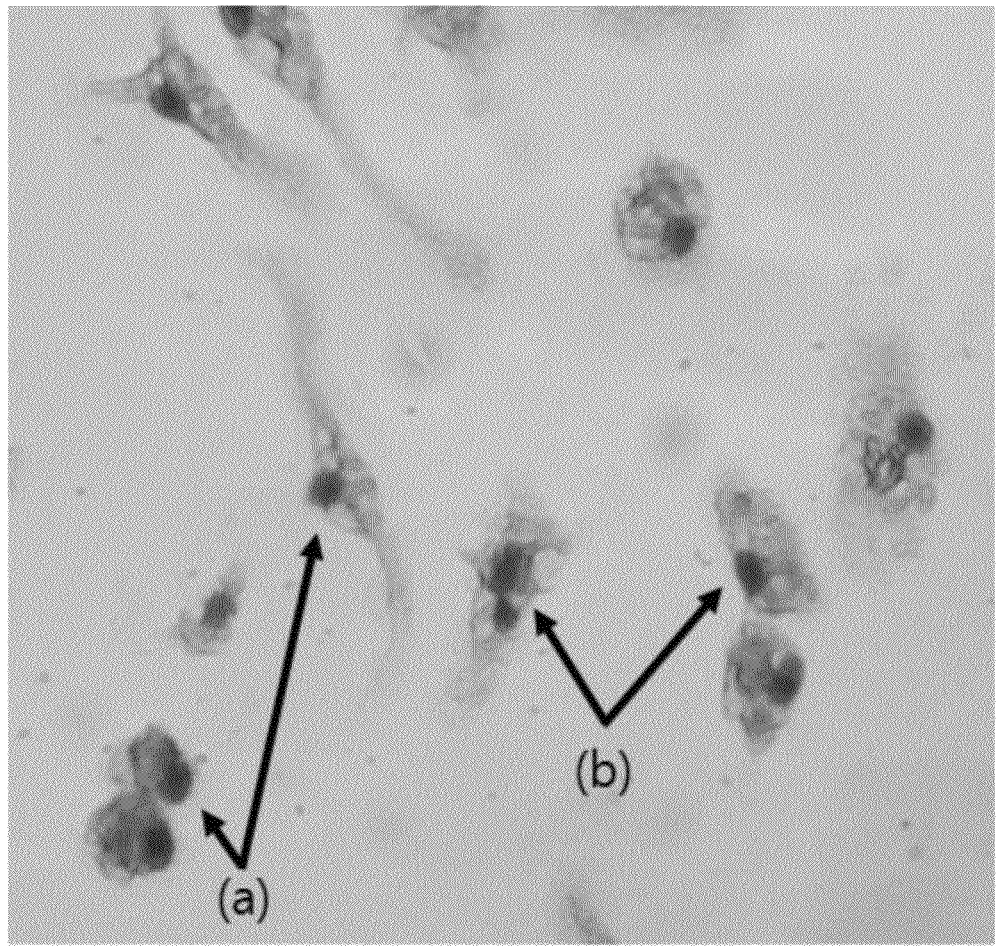
FIG. 16 shows resident macrophages (a) and macrophages activated by green tea-derived polysaccharides (b)

As can be seen from results, as compared to an untreated control group, GTW, GTE-0 and GTE-I activated about 20 macrophages at a concentration of 100 μg/mL, that is, caused no great activation, while GTE-II activated about 54 macrophages at a concentration of 100 μg/mL, that is, exhibited considerably superior macrophage activation (FIGS. 15 and 16).

Cytotoxicity of Activated Macrophages to Tumor Cells

In order to obtain macrophages activated by green tea-derived polysaccharide, 1 mL of 3% TG was abdominally injected, 200 μL of sample was administered at different concentrations after 24 hours to obtain macrophages, effector cells activated for 48 hours. B16BL6 melanoma cells were used as cancer cells (target cells) for measuring cytotoxicity of effector cells. That is, the effector cells and target cells were seeded on a flat-bottomed 96-well microplate such that the ratio of effector cells to target cells (E/T ratio) was adjusted to 10 to 20 and incubated at 37° C. in a 5% $CO_2$ incubator for 18 to 24 hours. After culturing, the culture plate was centrifuged at 1,500 rpm for 5 minutes and 100 μL of the cell culture medium supernatant was collected. LDH was separated from the target cells into the supernatant through killing capability of effector cells, NK cells, using an LDH assay kit. The tumor cell-killing capability (cytotoxicity, lysis) of NK cells was calculated by the following equation (Equation 2).

$$\text{Lysis (\%)} = \frac{E - S}{M - TSR} \times 100 \qquad \langle\text{Equation 2}\rangle$$

Figure 17:
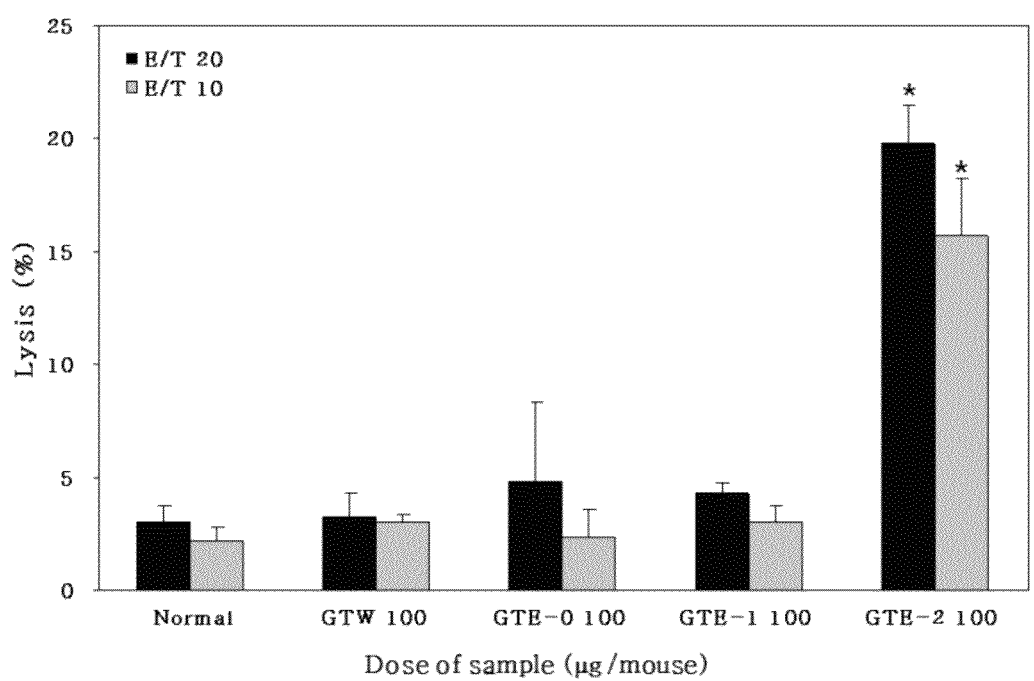
FIG. 17 shows ex vivo effects of green tea-derived GTW, GTE-I and GTE-II upon toxicity of mouse macrophages to cancer cells.

E—experimental release from effector cell,
S—average spontaneous release from target cell,
M—maximum release from target cell,
TSR—spontaneous release from target cell Considerable cancer cell-lysis activity was not induced in macrophages of normal group mice which were not treated with a sample and in macrophages of mice to which GTW, GTE-0 and GTE-I were administered at a concentration of 100 μg/mouse. However, it could be confirmed that macrophages of mice to which GTE-II was administered at a constant concentration of 100 μg/mouse exhibited lysis activity of about 18% and exhibited considerably high activity as compared to other samples (FIG. 17). This result and the result of test Example <4-2> demonstrated that GTW, GTE-0 and GTE-I activate NK cells having cell-killing capability (lysis) and activated NK cells mediate as anti-metastatic effector cells, GTE-II activates NK cells as well as macrophages, these two immune cells cooperate to exhibit high anti-metastatic activity.

As apparent from the fore-going, the food composition of the present invention is effective in boosting an immune function.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for boosting immune function comprising:
   administering to a subject in need thereof, a food composition containing a crude polysaccharide fraction of green tea which is prepared by treating green tea powder with an enzyme,
   wherein the green tea powder is made from mature green tea leaves and the enzyme is pectinase and does not comprise cellulase;
   centrifuging the resulting enzymatic hydrolysates to remove residues;
   adding ethanol to the resulting extract, followed by stirring to precipitate polysaccharide; and
   centrifuging the precipitated polysaccharide to obtain a crude polysaccharide fraction.

2. The method according to claim 1, wherein the crude polysaccharide fraction contains rhamnogalacturonan I and rhamnogalacturonan II as active components.

3. A preparation method of an immune-boosting food composition, the method comprising:
   treating green tea powder with an enzyme, wherein the green tea powder is made from mature green tea leaves and the enzyme is pectinase and does not comprise cellulase;

centrifuging the resulting enzymatic hydrolysates to remove residues;

adding ethanol to the resulting extract, followed by stirring to precipitate polysaccharide; and centrifuging the precipitated polysaccharide to obtain a crude polysaccharide fraction.

4. The preparation method according to claim 3, wherein adding ethanol comprises adding 95% ethanol.

5. The preparation method according to claim 3, wherein the crude polysaccharide fraction contains rhamnogalacturonan I or rhamnogalacturonan II.

* * * * *